(12) United States Patent
Ostrowski et al.

(10) Patent No.: US 12,304,407 B2
(45) Date of Patent: May 20, 2025

(54) NAVIGATIONAL ATTRIBUTE DRIVEN SYSTEM AND METHOD FOR ADJUSTING AN ADJUSTABLE COMPONENT OF A VEHICLE

(71) Applicant: Ford Global Technologies, LLC, Dearborn, MI (US)

(72) Inventors: David Alfred Ostrowski, Northville, MI (US); Leopoldo Urbina, Álvaro Obregón (MX); Akshay Dirisala, Olmsted Township, OH (US); Elizabeth Anne Manwell, Canton, MI (US); Austin Kirchner, Denver, CO (US)

(73) Assignee: Ford Global Technologies, LLC, Dearborn, MI (US)

( * ) Notice: Subject to any disclaimer, the term of this patent is extended or adjusted under 35 U.S.C. 154(b) by 333 days.

(21) Appl. No.: 17/543,078

(22) Filed: Dec. 6, 2021

(65) Prior Publication Data
US 2023/0174006 A1 Jun. 8, 2023

(51) Int. Cl.
| | |
|---|---|
| *B60R 16/037* | (2006.01) |
| *B60K 26/02* | (2006.01) |
| *B60N 2/02* | (2006.01) |
| *B60R 1/04* | (2006.01) |
| *B60R 1/07* | (2006.01) |
| *B60T 7/06* | (2006.01) |
| *B62D 1/187* | (2006.01) |

(52) U.S. Cl.
CPC ............ *B60R 16/037* (2013.01); *B60K 26/02* (2013.01); *B60N 2/0237* (2023.08); *B60N 2/0273* (2023.08); *B60N 2/0278* (2023.08); *B60R 1/04* (2013.01); *B60R 1/07* (2013.01); *B60T 7/06* (2013.01); *B62D 1/187* (2013.01); *B60K 2026/026* (2013.01); *B60N 2210/24* (2023.08); *B60N 2220/10* (2023.08); *B60N 2220/20* (2023.08)

(58) Field of Classification Search
CPC .......... B60R 16/037; B60R 1/04; B60R 1/07; B60K 26/02; B60K 2026/026; B60N 2/0244; B60N 2/0224; B60T 7/06; B62D 1/187; B62D 1/181; B62D 15/025; A61B 5/18
See application file for complete search history.

(56) References Cited

U.S. PATENT DOCUMENTS

| | | |
|---|---|---|
| 4,754,255 A | 6/1988 | Sanders et al. |
| 5,622,406 A | 4/1997 | Meschkat et al. |

(Continued)

FOREIGN PATENT DOCUMENTS

| | | |
|---|---|---|
| DE | 102018204826 A1 | 10/2019 |
| EP | 3343306 B1 | 12/2017 |

*Primary Examiner* — Isaac G Smith
*Assistant Examiner* — Nikki Marie M Molina
(74) *Attorney, Agent, or Firm* — Vichit Chea; Price Heneveld LLP

(57) ABSTRACT

Systems and methods are disclosed for supporting and executing automated control of adjustable components of a vehicle based on occupant classification in a group identity database. Methods and systems for generating and employing the group identity database are also disclosed. Occupancy information may be utilized to determine how the group identity database is employed.

19 Claims, 21 Drawing Sheets

(56) References Cited

U.S. PATENT DOCUMENTS

| | | | |
|---|---|---|---|
| 6,195,603 B1 | 2/2001 | Gauger et al. | |
| 8,725,311 B1 | 5/2014 | Breed | |
| 9,707,913 B1 | 7/2017 | Ochiai et al. | |
| 9,807,172 B2 | 10/2017 | Fan et al. | |
| 9,815,388 B1 | 10/2017 | Lindsay | |
| 10,046,671 B2 | 8/2018 | Seiller et al. | |
| 10,214,118 B1 | 2/2019 | Jain et al. | |
| 10,643,138 B2 | 5/2020 | Bellala et al. | |
| 11,428,540 B1 * | 8/2022 | Gray | G01C 21/3461 |
| 2014/0309790 A1 | 10/2014 | Ricci | |
| 2018/0345889 A1 * | 12/2018 | Pinkelman | B60N 2/002 |
| 2020/0164771 A1 | 5/2020 | Unnervik et al. | |
| 2020/0239004 A1 * | 7/2020 | Sobhany | B60N 2/0022 |
| 2021/0179117 A1 * | 6/2021 | Glazman | B60H 1/00357 |
| 2021/0331605 A1 * | 10/2021 | Lee | B60N 2/0228 |
| 2021/0354604 A1 * | 11/2021 | Migneco | A61B 5/18 |
| 2021/0380022 A1 * | 12/2021 | Kanitz | G06N 5/04 |

\* cited by examiner

NAVIGATIONAL ATTRIBUTE DRIVEN SYSTEM AND METHOD FOR ADJUSTING AN ADJUSTABLE COMPONENT OF A VEHICLE

FIELD OF THE DISCLOSURE

The present disclosure generally relates to a vehicle. More specifically, the present disclosure relates to adjustable components of a vehicle.

BACKGROUND OF THE DISCLOSURE

Vehicles often include settings for adjustable components. The settings can include at least one of a seat position, a mirror position, a steering component position, and a pedal assembly position.

SUMMARY OF THE DISCLOSURE

According to a first aspect of the present disclosure, a method for controlling at least one adjustable component of a vehicle includes receiving occupant data via at least one controller, the occupant data including demographic information corresponding to at least one occupant of the vehicle, receiving trip data via the at least one controller, the trip data including travel route information and occupancy information, the travel route information corresponding to a projected travel route and the occupancy information corresponding to at least one of a number of occupants, an identity of the at least one occupant, and a position of the at least one occupant, determining, via the at least one controller, fatigue estimation data corresponding to a projected fatigue of the at least one occupant along the projected travel route based on the trip data, and communicating, via an adjustment control system, an instruction to position the at least one adjustable component based on the fatigue estimation data.

Embodiments of the first aspect of the disclosure can include any one or a combination of the following features:
- the fatigue estimation data including target position data corresponding to at least one target position for the at least one adjustable component;
- adjusting the at least one adjustable component toward the at least one target position;
- the at least one adjustable component including at least one of a vehicle seat, a vehicle mirror, a steering component, and a pedal assembly;
- determining, based on the travel route information, trip segment data corresponding to at least one trip segment along the projected travel route via the at least one controller, the at least one trip segment including at least one travel segment profile metric having at least one of road type information, geographical information, topographical information, traffic density information, departure time information, arrival time information, and regulatory information;
- the at least one target position including a plurality of target positions and the at least one trip segment includes a plurality of trip segments, and the plurality of target positions corresponding to the plurality of trip segments.
- generating, via the adjustment control system, an instruction to position the at least one adjustable component from a first target position of the plurality of target positions toward a second target position of the plurality of target positions based on the vehicle moving from a first trip segment of the plurality of trip segments to a second trip segment of the plurality of trip segments;
- the fatigue estimation data being determined via access to a group identity database that includes a plurality of group identity profiles;
- applying a machine learning model trained with travel route information that is similar to the projected travel route;
- monitoring, via the at least one controller, a manual adjustment made to the at least one adjustable component away from the at least one target position; and
- updating the group identity database based on the manual adjustment via the at least one controller.

According to a second aspect of the present disclosure, a system for controlling at least one adjustable component of a vehicle includes at least one positioning actuator that adjusts the at least one adjustable component, an adjustment control system that controls the at least one positioning actuator, and at least one controller that receives occupant data, the occupant data including demographic information corresponding to at least one occupant of the vehicle, receives trip data, the trip data including travel route information and occupancy information, the travel route information corresponding to a projected travel route and the occupancy information corresponds to at least one of a number of occupants, an identity of the at least one occupant, and a position of the at least one occupant, determines fatigue estimation data corresponding to a projected fatigue of the at least one occupant along the projected travel route based on the trip data, and communicates, via the adjustment control system, an instruction to position the at least one adjustable component based on the fatigue estimation data.

Embodiments of the second aspect of the disclosure can include any one or a combination of the following features:
- the fatigue estimation data including target position data corresponding to at least one target position for the at least one adjustable component, and the at least one controller further controls the at least one adjustable component to adjust the at least one adjustable component toward the at least one target position;
- the at least one adjustable component including at least one of a vehicle seat, a vehicle mirror, a steering component, and a pedal assembly;
- the at least one controller including a controller on a personal mobile device of the at least one occupant and a local controller of the vehicle;
- trip segment data corresponding to at least one trip segment along the projected travel route, the at least one target position including a plurality of target positions and the at least one trip segment including a plurality of trip segments, and the plurality of target positions corresponds to the plurality of trip segments;
- the adjustment control system generating an instruction to position the at least one adjustable component from a first target position of the plurality of target positions toward a second target position of the plurality of target positions based on the vehicle moving from a first trip segment of the plurality of trip segments to a second trip segment of the plurality of trip segments;
- the fatigue estimation data being determined via access to a group identity database that includes a plurality of group identity profiles, and wherein the at least one controller applying a machine learning model with travel route information that is similar to the projected travel route;

the at least one controller monitoring a manual adjustment made to the at least one adjustable component away from the at least one target position; and the at least one controller updating the group identity database based on the manual adjustment.

According to a third aspect of the present disclosure, a system for controlling at least one adjustable component of a vehicle includes at least one positioning actuator that adjusts the at least one adjustable component, an adjustment control system that controls the at least one positioning actuator, a group identity database storing target position data corresponding to at least one target position for the at least one adjustable component, and at least one controller that receives occupant data, the occupant data including demographic information corresponding to at least one occupant of the vehicle, receives trip data, the trip data including travel route information and occupancy information, the travel route information corresponds to a projected travel route and the occupancy information corresponds to at least one of a number of occupants, an identity of the at least one occupant, and a position of the at least one occupant, communicates the occupant data and the trip data to the group identity database, receives, from the group identity database, the target position data determined based on the occupant data and the trip data, communicates, via the adjustment control system, an instruction to position the at least one adjustable component toward the at least one target position.

Embodiments of the third aspect of the disclosure can include any one or a combination of the following features:
the at least one adjustable component being at least one vehicle seat;
the at least one controller controlling the at least one positioning actuator to adjust the vehicle seat toward the at least one target position; and
the at least one controller including a controller on a personal mobile device of the at least one occupant and a local controller of the vehicle.

These and other aspects, objects, and features of the present disclosure will be understood and appreciated by those skilled in the art on studying the following specification, claims, and appended drawings.

DETAILED DESCRIPTION OF THE PREFERRED EMBODIMENTS

Figure 1:
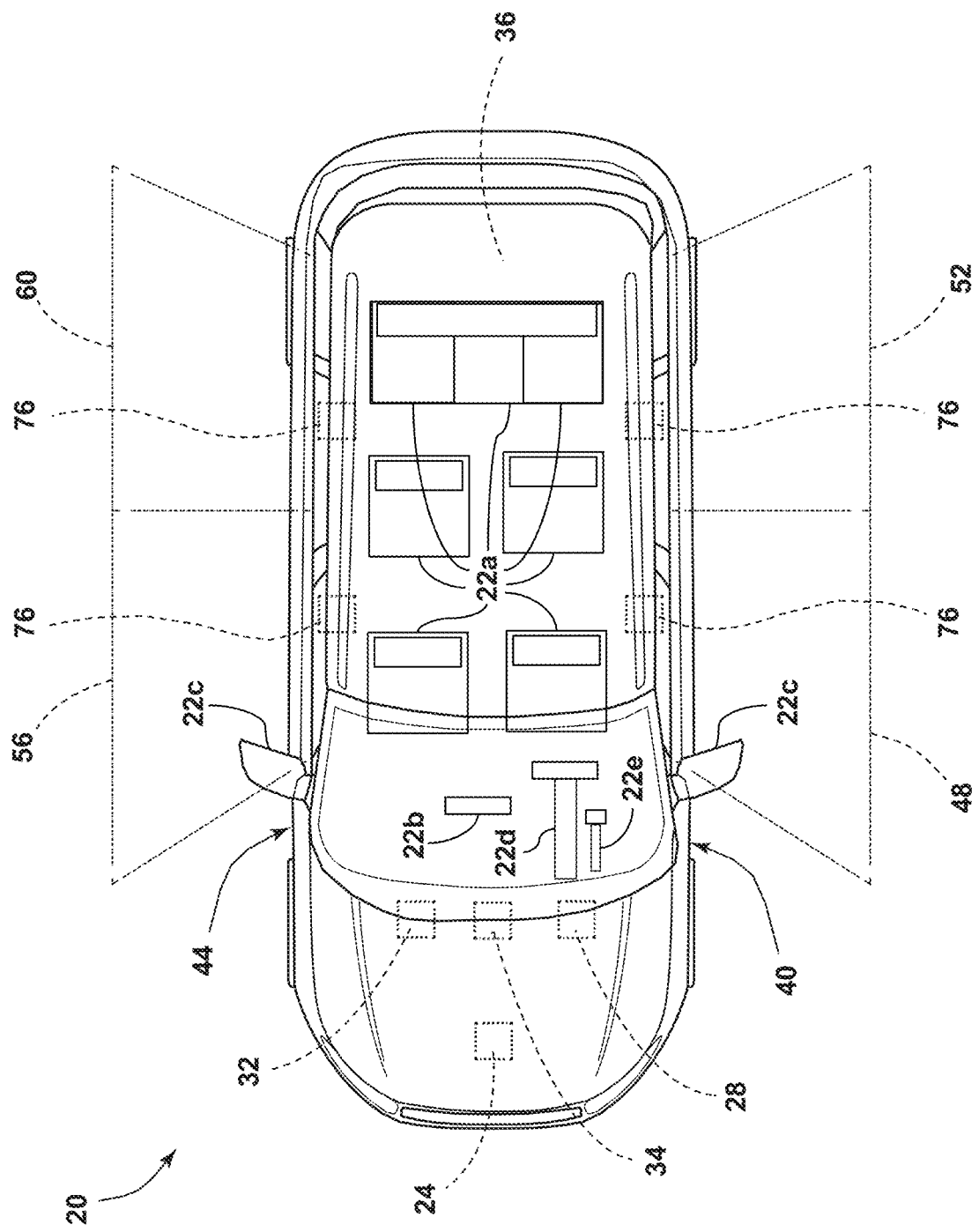
FIG. 1 is a top view of a vehicle illustrating a plurality of entry point zones according to one example.
Figure 2:
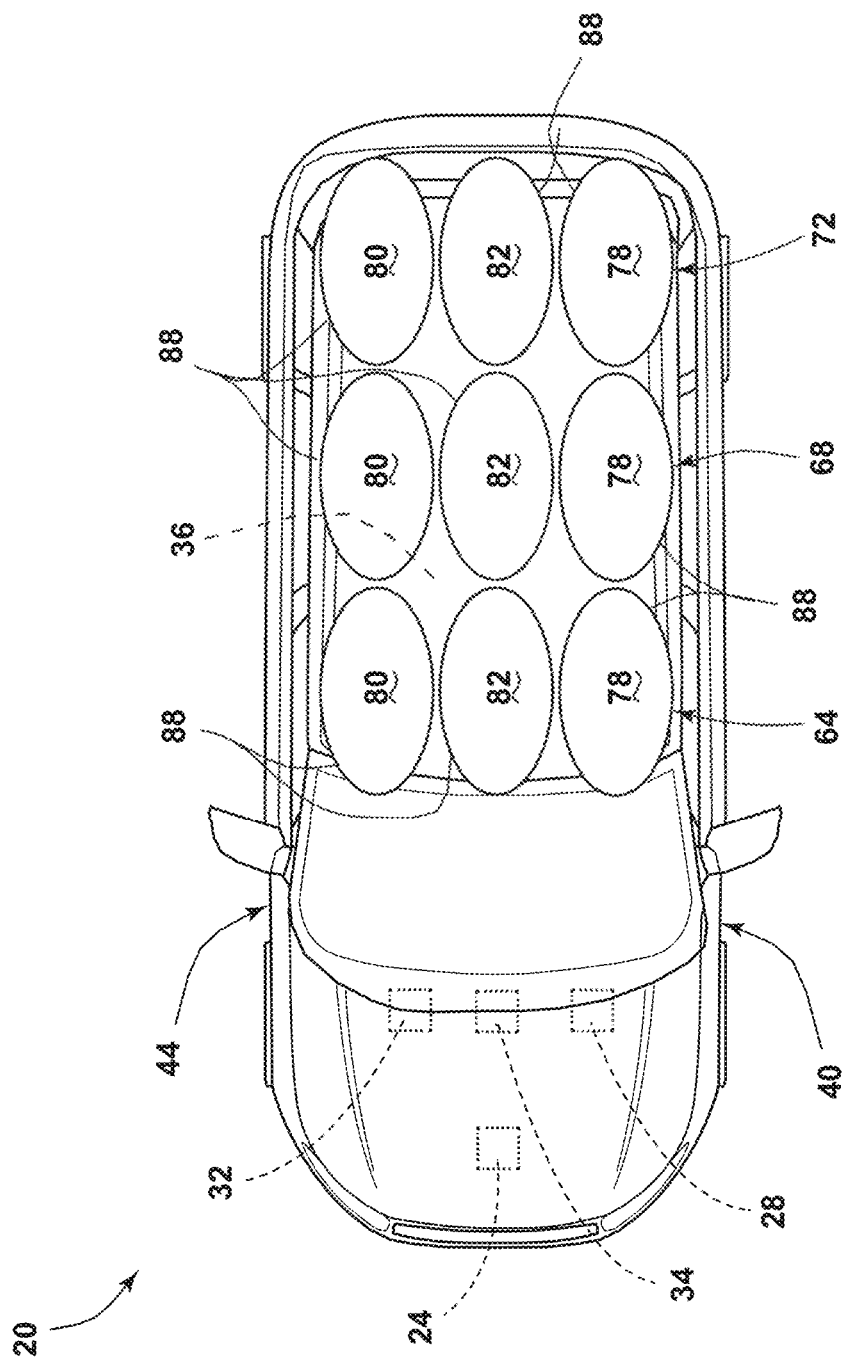
FIG. 2 is a top view of the vehicle illustrating occupant zones according to another example.
Figure 3:
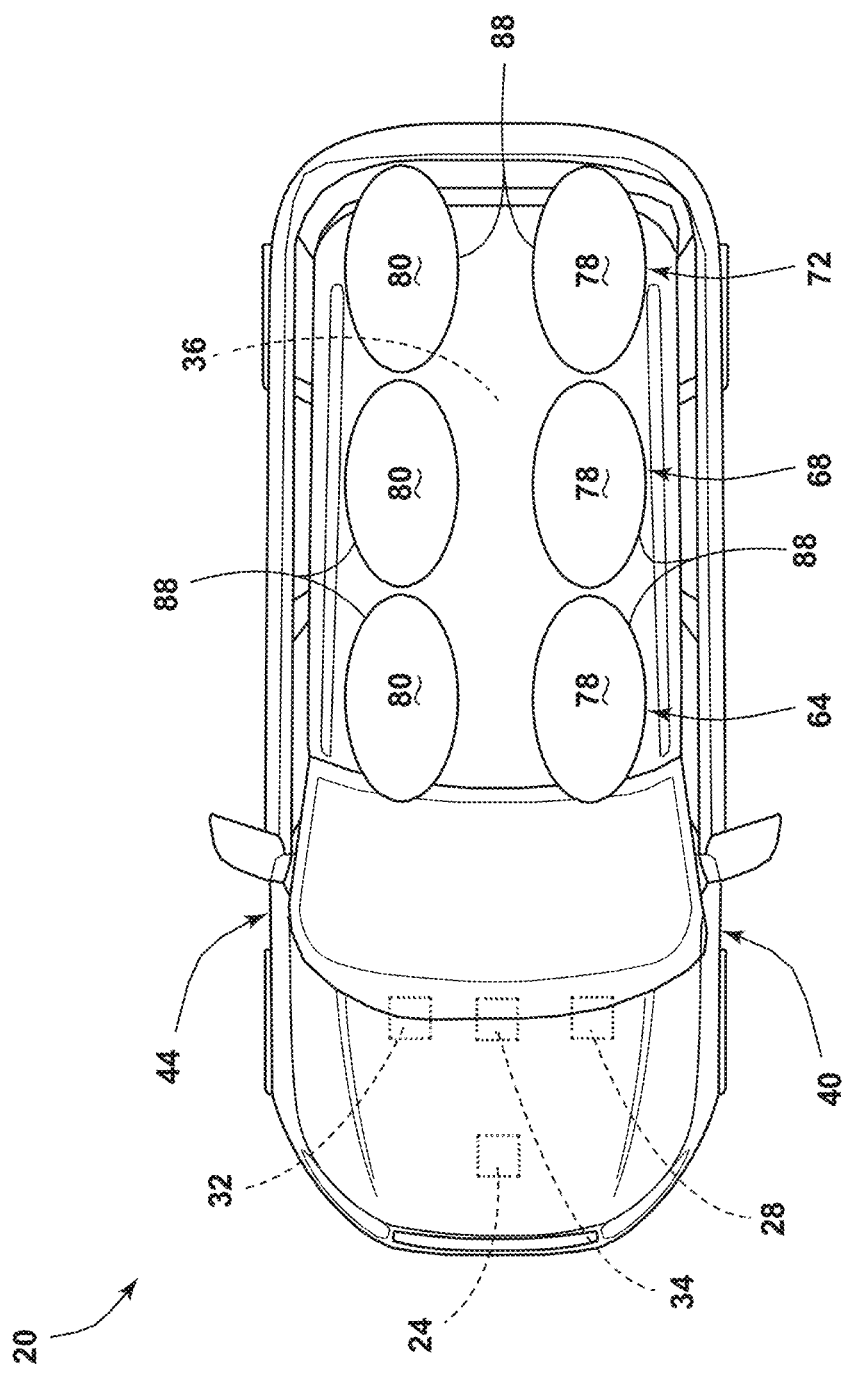
FIG. 3 is a top view of the vehicle illustrating the occupant zones according to another example.
Figure 4:
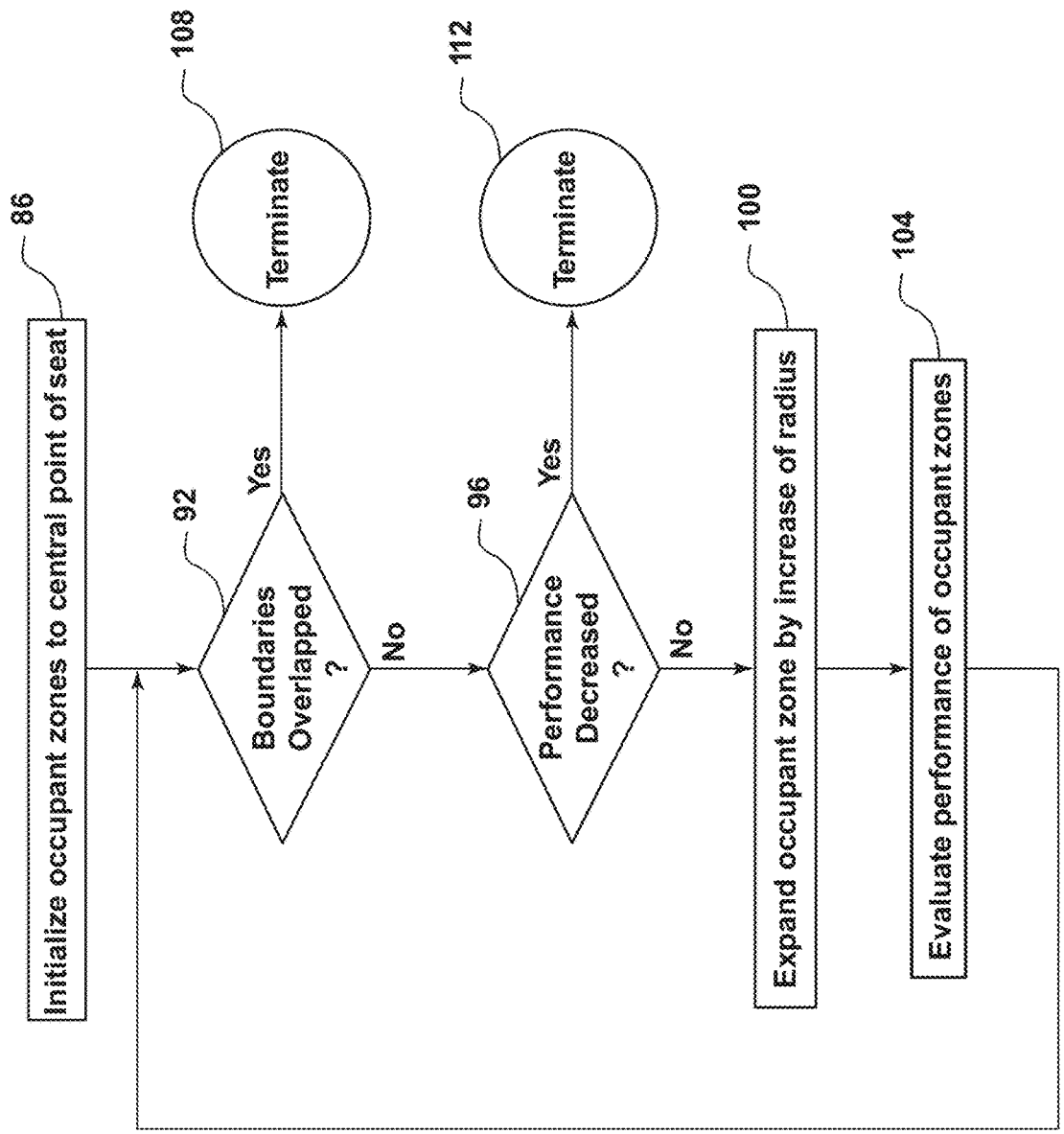
FIG. 4 is a flow diagram of a method of executing a trained model according to another example.

For purposes of description herein, the terms "upper," "lower," "right," "left," "rear," "front," "vertical," "horizontal," and derivatives thereof shall relate to the concepts as oriented in FIG. 1. However, it is to be understood that the concepts may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The present illustrated embodiments reside primarily in combinations of method steps and apparatus components related to adjustable components of a vehicle. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

As used herein, the term "and/or," when used in a list of two or more items, means that any one of the listed items can be employed by itself, or any combination of two or more of the listed items, can be employed. For example, if a composition is described as containing components A, B, and/or C, the composition can contain A alone; B alone; C alone; A and B in combination; A and C in combination; B and C in combination; or A, B, and C in combination.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. When the term "about" is used in describing a value or an end-point of a range, the disclosure should be understood to include the specific value or end-point referred to. Whether or not a numerical value or end-point of a range in the specification recites "about," the numerical value or end-point of a range is intended to include two embodiments: one modified by "about," and one not modified by "about." It will be further understood that the end-points of each of the ranges are significant both in relation to the other end-point, and independently of the other end-point.

The terms "substantial," "substantially," and variations thereof as used herein are intended to note that a described feature is equal or approximately equal to a value or description. For example, a "substantially planar" surface is intended to denote a surface that is planar or approximately planar. Moreover, "substantially" is intended to denote that two values are equal or approximately equal. In some embodiments, "substantially" may denote values within about 10% of each other, such as within about 5% of each other, or within about 2% of each other.

As used herein the terms "the," "a," or "an," mean "at least one," and should not be limited to "only one" unless explicitly indicated to the contrary. Thus, for example, reference to "a component" includes embodiments having two or more such components unless the context clearly indicates otherwise.

Referring to FIGS. 1-5, reference numeral 20 generally designates a vehicle. The vehicle 20 may be a motor vehicle. For example, the vehicle 20 may be a land-based vehicle (e.g., an automobile, a motorcycle, a train, etc.), an air-based vehicle (e.g., an airplane, a helicopter, etc.), and/or a water-based vehicle (e.g., a boat or other watercraft). While the vehicle 20 may be a motor vehicle, the present disclosure is not limited to internal combustion engines as a source of locomotive power for the vehicle 20. Rather, alternative sources may be utilized in providing locomotive power to the vehicle 20. For example, locomotive power may be provided to the vehicle 20 by electric motors, fuel cells, and/or petroleum-based fuel engines. According to various examples, the vehicle 20 may be driver-controlled, semi-autonomous, fully-autonomous, or any combination of user-controlled and automated. For example, the semi-autonomous example of the vehicle 20 may perform many or all-commuting functions (e.g., accelerating, braking, turning, signaling, etc.) independent of user interaction while the user maintains override control of the vehicle 20. It is generally contemplated that the term user can refer to an occupant of the vehicle 20, such as a driver of the vehicle 20 or a non-driver passenger of the vehicle 20.

Referring again to FIGS. 1-5, the vehicle 20 includes at least one adjustable component 22. The at least one adjustable component 22 may include various in-cabin and out-of-cabin parts such as a vehicle seat 22a, a rear-view mirror 22b, a side mirror 22c, a steering component 22d, and a pedal assembly 22e. The vehicle 20 includes an adjustment control system 24 that can adjust the at least one adjustable component 22 to provide ergonomic support to at least one occupant 26 of the vehicle 20. It is appreciated that the adjustment control system 24 may include a controller, and may further be referred to herein as a controller 24 when referencing one or more of the controllers discussed herein. For example, a vehicle-based controller 28 may be stored on the vehicle 20 and include a processor and memory. The memory can store software routines that are executable by the processor. In various situations, some of which will be discussed further herein, the software routines within the memory may be accessed by the vehicle-based controller 28 and/or the processor in response to an input (e.g., from the vehicle 20 and/or the user). The vehicle-based controller 28 is coupled to the vehicle 20 such that the vehicle-based controller 28 is moved through space as the vehicle 20 moves through space. Said another way, the vehicle-based controller 28 is carried by the vehicle 20.

At least one positioning actuator 30 may be positioned about the at least one adjustable component 22 for adjusting the at least one adjustable component 22. For example, and with reference to FIG. 5, the at least one positioning actuator 30 may include a first positioning actuator 30a positioned adjacent a portion of the vehicle seat 22a, a second positioning actuator 30b positioned adjacent a portion of the rear-view mirror 22b, a third positioning actuator 30c positioned adjacent a portion of the side mirror 22c, a fourth positioning actuator 30d positioned adjacent a portion of the steering component 22d, and a fifth positioning actuator 30e positioned adjacent a portion of the pedal assembly 22e. The at least one positioning actuator 30 may include an electric motor, an air pump having a bladder 31, a solenoid, and/or another electro-mechanical adjustment device. According to some aspects of the present disclosure, the at least one positioning actuator 30 may be controlled to position the vehicle seat 22a closer or further from any one of the rear-view mirror 22b, the side mirror 22c, the steering component 22d, and the pedal assembly 22e. It is generally contemplated that the pedal assembly 22e may be a brake pedal assembly for controlling a braking system of the vehicle 20 or a gas pedal assembly for controlling delivery of fuel to an engine of the vehicle 20.

According to some examples, the vehicle seat 22a may include various adjustment parameters controlled via the adjustment control system 24, including but not limited to backrest angle, cushion edge, fore-and-aft positions, head support angle, head support level, seat depth, seat height, shoulder support, variable head support, cushion tilt, seat message, side bolster settings, and lumbar support. The steering component 22d may also include various adjustment parameters controlled via the adjustment control system 24, such as vertical (e.g., rake) position, and telescopic position (e.g., the steering wheel closer to/further from the vehicle seat 22a). The mirrors 22b, 22c may also include various adjustment parameters controlled via the adjustment control system 24, such as horizontal and vertical tilt angles.

Referring further to FIGS. 1-5, the vehicle 20 may be provided with a Global Positioning System (GPS) 32 and an occupancy detection system 34. The occupancy detection system 34 may comprise a portion of the vehicle-based controller 28 or may be a separate component in communication with the vehicle-based controller 28 and receives information related to the at least one occupant 26 present in a cabin 36 of the vehicle 20. The vehicle 20 can be provided with a plurality of entry points for passengers, users, or occupants. For example, at least one of the plurality of entry points can be positioned on a driver's side 40 of the vehicle 20. Similarly, at least one of the plurality of entry points can be positioned on a passenger's side 44 of the vehicle 20. While the terms "driver's side" and "passenger's side" are used to distinguish a first side of the vehicle 20 from a second side of the vehicle 20, these terms are not intended to be limiting. For example, when the vehicle 20 is fully-autonomous, conventional operator controls may be omitted from the cabin 36 such that an occupant seated on the driver's side 40 and in a forward-most row of the vehicle 20 may not be actively driving the vehicle 20. The driver's side 40 and the passenger's side 44 may each be provided with one or more access doors through which an occupant or occupants may enter or exit the cabin 36. The one or more access doors may be monitored via the occupancy detection system 34 to determine a point of entry for a given occupant and/or a number of occupants that have entered a given access door. For example, if the driver's side 40 and the passenger's side 44 are each provided with two access doors, then the driver's side 40 can be provided with a first entry point zone 48 and a second entry point zone 52 while the passenger's side 44 is provided with a third entry point zone 56 and a fourth entry point zone 60. The first and third entry point zones 48, 56 may be associated with a first row of seats 64 in the cabin 36. The second and fourth entry point zones 52, 60 may be associated with a second row of seats 68 and/or a third row of seats 72. The first, second, third, and fourth entry point zones 48, 52, 56, 60 may be monitored independently. For example, a monitoring device 76 may be positioned proximate to each of the access doors.

Referring yet again to FIGS. 1-5, identifying the point of entry of a given occupant or user can be beneficial in determining which row of seats the individual is likely to be occupying and/or which seating assembly within the rows of seats 64, 68, 72 the individual is likely to be occupying. Additionally, or alternatively, the occupancy detection system 34 can identify the point of entry of a given occupant or user as a cross-reference with additional data to determine a specific location of an individual user or occupant. For example, proximity sensors, RSSI antennae, weight sensors, seat strap latch sensors, and the like may be employed within the cabin 36 to identify occupied seating assemblies. It is contemplated that the vehicle-based controller 28 may be provided with an arrangement of the seating assemblies within the cabin 36 of the vehicle 20 and/or the vehicle-based controller 28 may be provided with a list of possible arrangements of the seating assemblies within the cabin 36 of the vehicle 20. The information with regard to the arrangement, or possible arrangements, of the cabin 36 can aid in establishing a number of seating positions. For example, each of the rows of seats (e.g., the first row of seats 64, the second row of seats 68, and/or the third row of seats 72) may be provided with a first seat 78, a second seat 80, and/or a third seat 82.

Referring again to FIGS. 1-5, the first seat 78 may be positioned nearest to the driver's side 40 of the vehicle 20. The second seat 80 may be positioned nearest to the passenger's side 44 of the vehicle 20. The third seat 82 may be positioned between the first and second seats 78, 80, for example, as a middle seat. By "knowing" the available seating positions, at least one of the vehicle-based controller 28 and the occupancy detection system 34 may be better enabled to determine a location of a given occupant and/or distinguish between adjacent occupants. For example, the vehicle-based controller 28 and/or the occupancy detection system 34 may be capable of determining a number of personal devices (e.g., smartphones, smartwatches, or other wearable/carry-able smart-enabled technologies) within the cabin 36 by referencing one or more inputs from sensors of the vehicle 20. The location of a given one of the personal devices may be determined, for example, by triangulation or trilateration with RSSI antennae. The determined location of the given one of the personal devices may then be compared with the "known" seating positioned of the vehicle 20. In the event that the determined location of the given one of the personal devices does not reside within one of the "known" seating positions, additional steps may be taken in an effort to refine the determined location and/or the "known" seating positions.

The occupancy detection system 34 may receive occupant data that includes identification information and demographic information corresponding to the at least one occupant 26. For example, the occupant data may include age, sex, name, race, familial status, height, and weight information, as well as various preferential information, such as hobby interests, musical preferences, and the like. It is generally contemplated that the occupant data can further include any information stored on the occupant's smart device, such as a smartphone, including social media information and preferences, the occupant's name, domicile, place of work, and the like. In some examples, the identification information may include an identity of a first occupant and an identity of a second occupant of the vehicle 20. The occupant data can have varying levels of specificity as to the identity or demographic information corresponding to the at least one occupant 26. By way of example, if the at least one occupant 26 is a married, 35-year-old father of four children, being six feet tall, weighing 200 pounds, and named "John Smith," the occupant data may only utilize one aspect (e.g., "male") or may utilize several aspects (e.g., "35-year-old father").

Referring now to FIGS. 2-6, in determining a location of a given occupant, or an occupant's personal device, a trained model may be employed. The trained model can be executed on the vehicle-based controller 28 and/or a controller that is in communication with the vehicle-based controller 28 (e.g., a controller on the user's personal device, a controller that is remote from the vehicle 20, a cloud-based controller, etc.). It is generally contemplated that the occupancy detection system 34 or the vehicle-based controller 28 can determine a current occupancy configuration from a plurality of occupancy configurations of the vehicle 20 by utilizing the trained model. An occupancy configuration may refer to a seating position arrangement of and/or an identity of the plurality of occupants in the vehicle 20. As a starting point, a method 84 of executing the trained model may begin with step 86 of initializing an occupant zone to a central point of each "known" seating position. The occupant zones can each have a boundary 88. Once the occupant zones have been initialized at each of the "known" seating positions, the method 84 advances to decision point 92, where the method 84 determines if adjacent ones of the boundaries 88 of the initialized occupant zones overlap with one another. If, at decision point 92, the method 84 determines that the boundaries 88 of adjacent initialized occupant zones do not overlap, then the method 84 advances to decision point 96. At decision point 96, the method 84 determines whether performance of locating the occupant 26, or the occupant's personal device, to a "known" seating position has decreased. For example, a distance between the occupant 26, or the occupant's personal device, and the boundaries 88 may be monitored. If the distance between the occupant 26, or the occupant's personal device, and the boundaries 88 has decreased or stayed the same when compared to the initialized occupant zone, then decision point 96 would indicate that the performance of the locating of the occupant 26, or the occupant's device, to one of the "known" seating positions has not decreased.

Referring again to FIGS. 2-6, if the method 84 determines at decision point 96 that the performance of locating the occupant 26, or the occupant's personal device, to a "known" seating position has not decreased (i.e., improved or stayed the same), then the method 84 advances to step 100 of expanding the boundaries 88 of the occupant zones by increasing a radius of the boundaries 88. In examples where the boundaries 88 are defined by more than one axis (e.g., an ellipse with a major axis and a minor axis), then the axes may be increased sequentially or simultaneously. Similarly, the axes may be increased at varied rates. For example, the major axis may extend in a longitudinal direction (i.e., front-to-rear) of the vehicle 20 and may be increased at a faster rate than the minor axis, which may extend in a lateral direction (i.e., side-to-side) of the vehicle 20. In so doing, a surface area and/or volume covered by the boundaries 88 may be increased in a manner that decreases a chance of capturing an adjacent occupant or an adjacent occupant's personal device. Therefore, inaccurately assigning an occupant 26 to a given "known" seating position may be more readily avoided. A performance of the locating of the occupant 26, or the occupant's device, to one of the "known" seating positions is evaluated at step 104. As with decision point 96, a distance between the occupant 26, or the occupant's personal device, and the boundaries 88 can be evaluated at step 104.

Once the performance of the expanded boundaries 88 of the occupant zones have been evaluated at step 104, the method 84 can return to decision point 92 and repeat the method 84 in an iterative manner. The method 84 may be terminated at step 108 when the boundaries 88 have been determined to overlap at decision point 92 or at step 112 when the performance evaluated at decision point 96 has decreased. In the event that the boundaries 88 have been determined to overlap and/or the performance has decreased, the method 84 may revert back to the immediately preceding boundaries 88 to avoid such overlap and/or such a decrease in performance. Once the boundaries 88 of the occupant zones have been established and the occupant 26, or the occupant's personal device, has been located to one of the "known" seating positions, one or more adjustable components 22 of the vehicle 20 may be monitored for the individual in the given "known" seating position. The one or more adjustable components 22 can include, but are not limited to, the vehicle seat 22a, a vehicle mirrors 22b, 22c, a steering component 22d, a gas or brake pedal, and the like.

Figure 6:
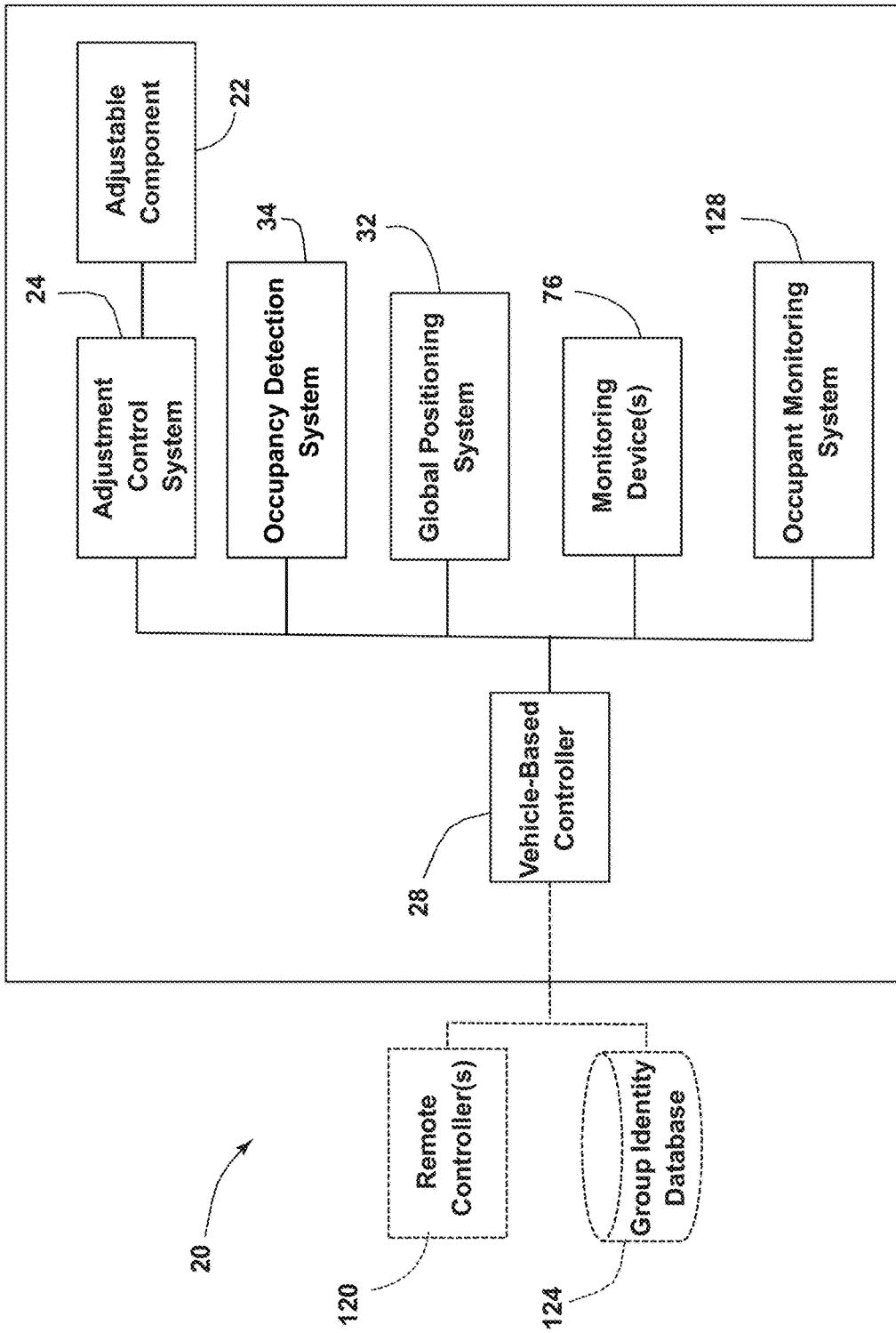
FIG. 6 is a block diagram of the vehicle and components that are in communication with a vehicle-based controller according to another example.

Referring to FIG. 6, the vehicle 20 includes the vehicle-based controller 28. The vehicle-based controller 28 is in communication with the adjustment control system 24. The adjustment control system 24 can adjust at least one adjustable component 22 of the vehicle 20 (e.g., adjusting a current and/or a voltage supplied to the at least one positioning actuator 30). The monitoring device(s) 76 are also in communication with the vehicle-based controller 28 and/or the occupancy detection system 34. Further, the vehicle-based controller 28 is in communication with the Global Positioning System (GPS) 32. In various examples, the vehicle-based controller 28 can be in communication with one or more remote controllers 120. The one or more remote controllers 120 can include a processor and memory. The memory can store software routines that are executable by the processor. In various situations, some of which will be discussed further herein, the software routines within the memory may be accessed by the one or more remote controllers 120 and/or the processor in response to an input (e.g., from the vehicle 20 and/or the user). The one or more remote controllers 120 can include, but are not limited to, a controller 120 on the occupant's personal device (e.g., smartphone, smartwatch, etc.), a cloud-based controller, and/or a controller on a server at a location that is remote from (i.e., not on-board) the vehicle 20. The vehicle-based controller 28 is also in communication with a group identity database 124. The group identity database 124 may be stored within the vehicle-based controller 28 (e.g., within memory of the vehicle-based controller 28). Alternatively, the group identity database 124 may be stored at a location that is remote from the vehicle 20, such as on a remote computing device (e.g., computer, server, or the like).

Referring again to FIG. 6, the group identity database 124 can include information from a user pool. The user pool can include individuals, or groups of individuals, that have interacted with the vehicle 20 in the past, individuals, or groups of individuals, that have interacted with another vehicle that is equipped with the features discussed herein, historical datasets of individual preferences that were obtained by market research, individuals, or groups of individuals, who are actively using another vehicle that is equipped with the features discussed herein, and so on. It is generally contemplated that the group identity database 124 can include information related to different makes and models of vehicles, and that the user pool can include individuals, or groups of individuals, that have interacted with the different makes and models of vehicles similar to or different than the make and model of vehicle 20. The information stored in the group identity database 124 can include demographic information of individuals in the user pool, geographic information of individuals in the user pool, situational information of individuals in the user pool, and the like. The term situational information, as used herein, is intended to broadly refer to a variety of "if-then" scenarios. For example, the situational information of the individuals within the user pool can include information about a number of passengers within the cabin 36, information about the identities of the passengers (e.g., a group of individuals that commonly travels together, familial relationship, etc.), information about a number of rows of seats within the cabin 36, a type of driving undertaken (e.g., city, highway, rural, straight sections of road, curved sections of road, etc.), an average speed of the vehicle 20 during use, an average time when the vehicle 20 is stopped (e.g., as a metric of idle time or a metric relating to traffic), an amount of time below a threshold speed, an amount of time above a threshold speed, and so on. Furthermore, the situational information may include fatigue estimation data corresponding to a projected fatigue of at least one occupant 26, as well as anxiety data corresponding to a projected anxiety of the at least one occupant 26.

The group identity database 124 can include a plurality of group identity profiles associated with identification information of a given occupant. The plurality of group identity profiles can correspond to the plurality of occupancy configurations. By way of example, a driver of the vehicle 20 may have a first group identity profile corresponding to a first occupancy configuration, a second group identity profile corresponding to a second occupancy configuration, and a third group identity profile corresponding to a third occupancy configuration. Continuing with this example, first occupancy configuration can correspond to a first occupant being a driver and the only occupant of the vehicle 20, the second occupancy configuration can correspond to the first occupant being the driver, a second occupant being the driver's spouse in the front passenger seat, and the third group identity profile can correspond to the first occupant being a driver, the second occupant being the driver's spouse positioned in the front passenger seat, and the driver's child (i.e., a third occupant) being positioned in a rear bench seat. In this example, each of group identity profiles that corresponds to the given occupancy configuration can include different or similar target position data for the at least one adjustable component 22 (e.g., the at least one vehicle seat 22a). It is generally contemplated that the group identity profiles can have a plurality of levels of generality for the same occupancy configuration of the vehicle 20, such as "Husband driver, wife front-passenger," "Driver, one passenger," and "Driver, at least one passenger." Said differently, the term group identity profile can refer to specific identities of the occupants of the vehicle 20 (e.g., "John Smith and Jill Jones"), relative identities of the occupants of the vehicle 20 (e.g., "friends, "family," "Grandson and Grandma," etc.), or merely a number of occupants of the vehicle 20 (e.g. "Driver with no other passengers"). The level of generality associated with the group identity profiles that is most helpful for reducing fatigue and improving ergonomic support can be determined based on the iterative training of the trained models. In other words, the at least one controller 24, 28, 120 can be operable to identify the degree to which an aspect of the current occupancy configuration affects the overall preferred positions of the at least one adjustable component 22.

Referring further to FIG. 6, the vehicle-based controller 28 may, additionally or alternatively, be in communication with an occupant monitoring system 128. The occupant monitoring system 128 can include a camera, a microphone, and/or the user's personal device. In general, the occupant monitoring system 128 seeks to observe the occupant 26 or user in an effort to gauge or infer a degree of anxiety. For example, the camera may collect images of a face 188 of the user and evaluate the images by employing image-based emotional mapping, as will be discussed in further detail herein. In some examples, Viola-Jones object detection framework can be employed in categorizing emotions of the user. The microphone may be used to monitor a voice of the user. For example, the microphone may monitor a tone in the voice of the user, words uttered by the user, and/or a volume (e.g., decibels) of the voice of the user. In examples where the user's personal device is capable of monitoring vital signs (e.g., EEG, EKG, heartrate, blood pressure), such as a smartwatch or smart wearable, such information can be employed as an input in gauging or inferring the degree of anxiety of the user.

Referring still further to FIG. 6, the information gathered by the occupant monitoring system 128 may be transmitted to the group identity database 124 for storage and/or classification. It is contemplated that the vehicle-based controller 28 and/or one or more of the remote controllers 120 may be employed in analyzing and/or classifying the information provided by the adjustment control system 24, the Global Positioning System (GPS) 32, the monitoring device(s) 76, the occupancy detection system 34, and/or the occupant monitoring system 128. The group identity database 124 aggregates the information of the user pool and the at least one occupant 26. The vehicle-based controller 28, the remote controller(s) 120, and/or the group identity database 124 can be provided with one or more trained models that evaluate behavior of the user or occupant of the vehicle 20 and seek to group the user with an aligned cohort from the user pool. Aligned cohort, as used herein, is intended to refer to a group of individuals from the user pool that behave, are predicted to behave, or have behaved, similarly to the user in a given circumstance or situation, as will be discussed further herein. As such, it is generally contemplated that the aligned cohort can utilize the plurality of group identification profiles to group the user with the aligned cohort. The behavior of the aligned cohort can be employed to infer a target position for the at least one adjustable component 22, such as a vehicle seat position, for the user in a given circumstance or situation. In the event that the user departs from the target position, the trained model(s) can update and/or refine the aligned cohort in an effort to decrease a probability of user deviation from the target position.

Figure 7:
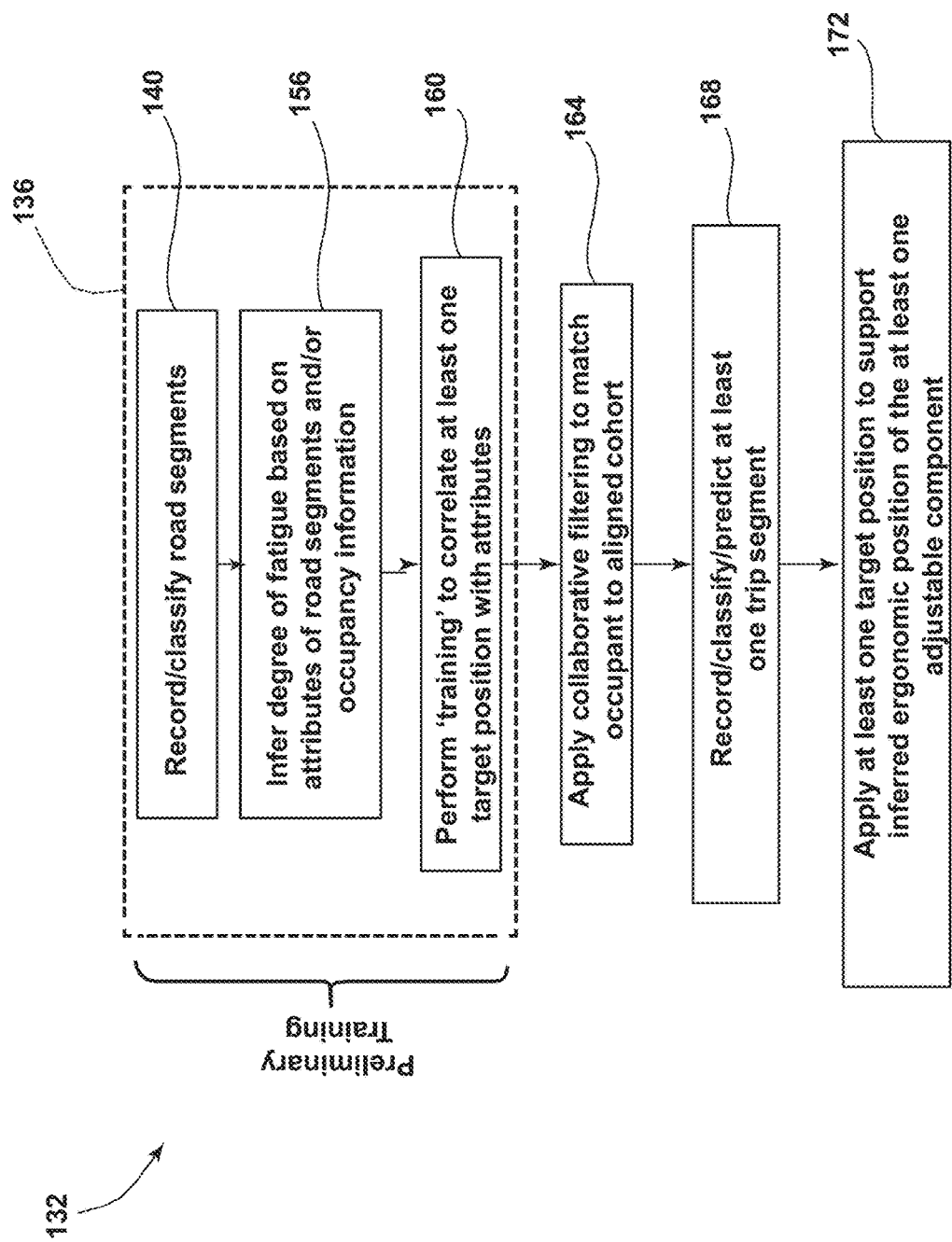
FIG. 7 is a flow diagram of a method for adjusting at least one adjustable component according to another example.
Figure 8:
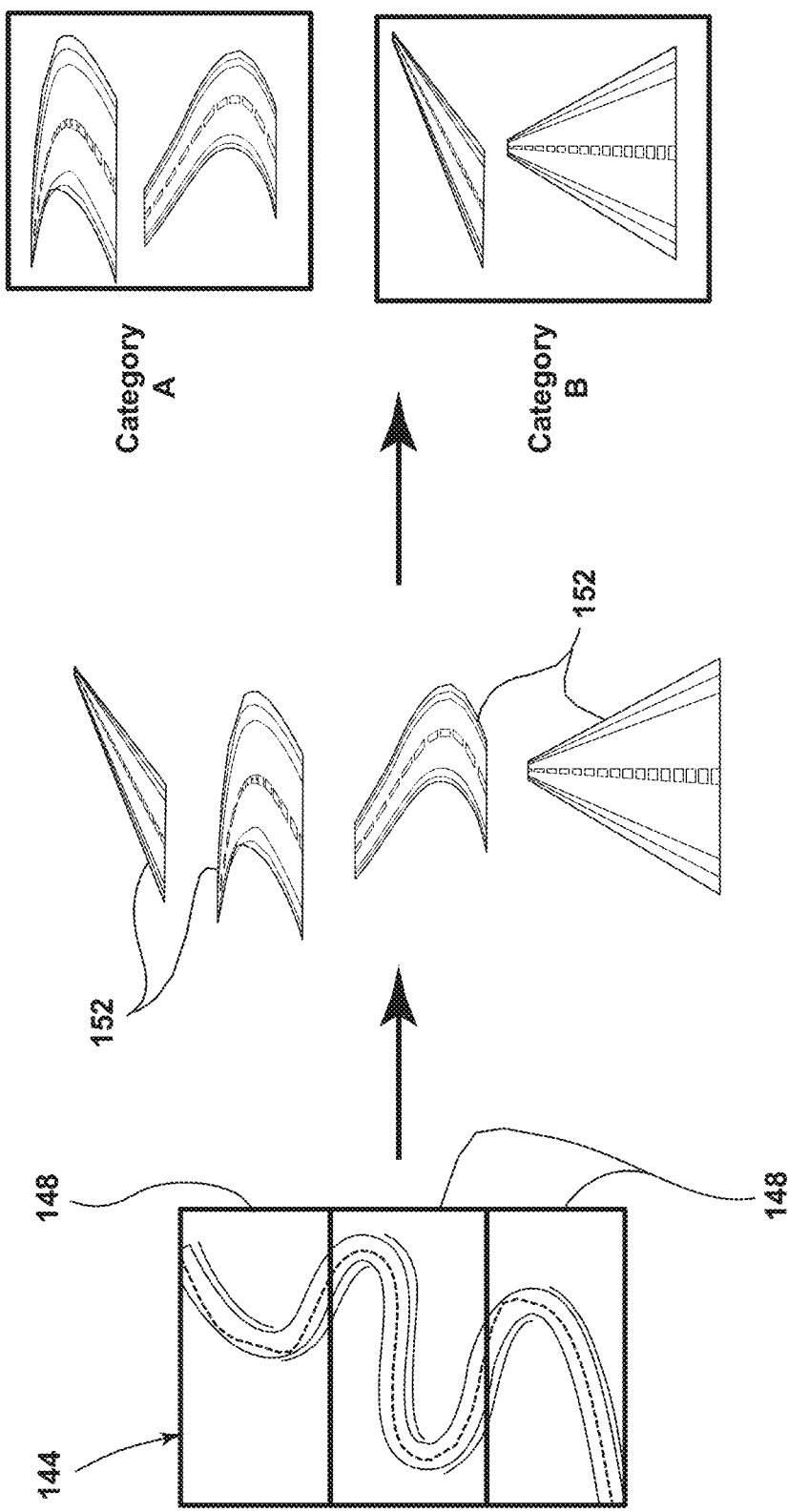
FIG. 8 is a flow diagram depicting a travel route being separated into trip segments, according to another example.

Referring now to FIGS. 6-8, one or more of the group identity database 124, the remote controller 120, and the vehicle-based controller 28 can be employed to determine or predict travel route information corresponding to a projected travel route. The projected travel route can be predicted based on the occupancy information and the occupant data. More particularly, the projected travel route may be predicted based on prior use of the vehicle 20 by the at least one occupant 26, or by other users of the user pool stored in the group identity database 124. For example, if a desired route is not detected by the GPS 32 (i.e., not entered by the at least one occupant 26 or provided via synchronization of a smart device with the vehicle-based controller 28), the group identity database 124 may be utilized to provide a prediction as to the likely destination of the vehicle 20 at the end of the trip, as well as likely travel routes to the likely destination. The travel route information may comprise a portion of the data received by at least one controller 24, 28, 120. This data may be referred to as trip data, with the trip data comprising the travel route information and the occupancy information. In other words, the trip data can encompass not only the various aspects of the travel route of the vehicle 20, but also various aspects of the occupants in the vehicle 20. In this way, the trip data can be employed to provide a more comprehensive correlation to the projected anxiety and/or the projected fatigue of the at least one occupant 26. By ascertaining the relationship between anxiety, ergonomics, the trip data, and/or fatigue of the occupant(s), at least one target position for the at least one adjustable component 22 is better approximated. Additionally or alternatively, the Global Positioning System (GPS) 32 can be employed by the at least one controller 24, 28, 120 to receive the projected travel route (e.g., a planned travel route).

The at least one controller 24, 28, 120 can utilize the Global Positioning System (GPS) 32 to classify at least one trip segment 148 along the projected travel route. The projected travel route may be mapped between a current location of the vehicle 20 and an intended destination of the vehicle 20, which can be input by the at least one occupant 26. The projected travel route may be an active monitoring of driving conditions and/or driving maneuvers that are currently being executed when an intended destination is not input by the at least one occupant 26. For example, the current travel route may be monitored by referencing a forward-facing camera on the vehicle 20, a speed of the vehicle 20, a rotational angle of steering components of the vehicle 20, and so on in an effort to infer attributes 152 of the projected travel route.

A method 132 for controlling the at least one adjustable component 22 is depicted according to one example (see FIG. 7). The method 132 can include a preliminary training stage 136. In the preliminary training stage 136, the method 132 executes step 140 of classifying at least one trip segment 148. Classification of the trip segment 148 of the at least one trip segment 148 at step 140 can be accomplished in the active manner described above and/or by evaluating the projected travel route. The trip segment 148 can be classified based on the attributes 152 of the trip segment 148 (e.g., curved road, straightaways, city, highway, rural, high traffic, low traffic, etc.). For example, as depicted in FIG. 7, a travel route 144 (planned or current) can be divided into trip segments 148. The trip segments 148 can be evaluated to determine their attributes 152. The attributes 152 can be categorized based on similarities in features and/or similarities in user responses to such attributes 152 (e.g., anxiety level, fatigue level, probability for highway hypnosis, etc.). For example, the attributes 152 may be placed in Category A if they are likely to result in increased anxiety or fatigue, and the attributes 152 may be placed in Category B if they are less likely to result in increased anxiety or fatigue. In such an example, the likelihood of increased anxiety or fatigue in Category A may also be categorized as less likely to result in highway hypnosis. Similarly, the lower likelihood of increased anxiety or fatigue in Category B may also be categorized as more likely to result in highway hypnosis.

Figure 5:
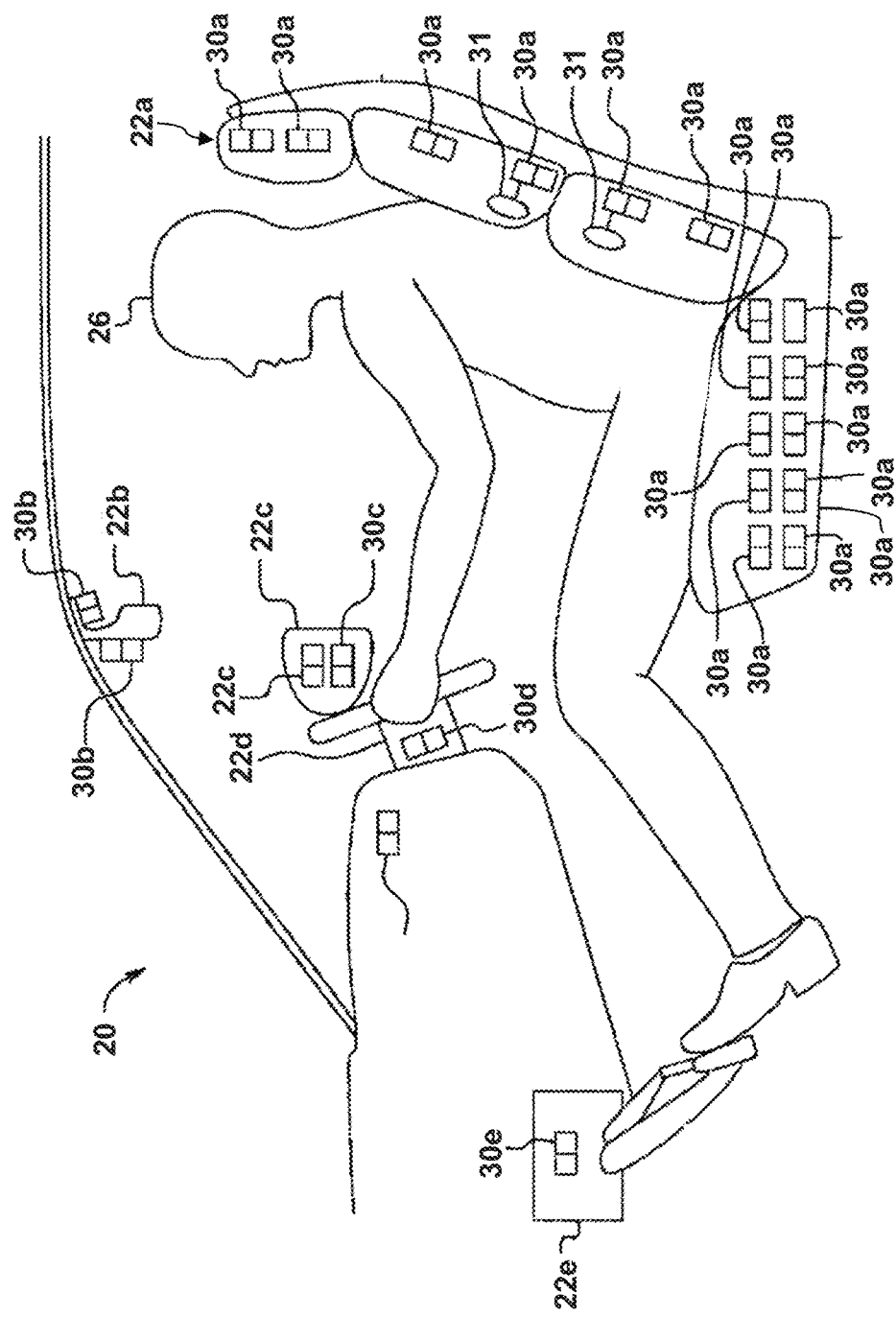
FIG. 5 is a side cross-sectional view of the vehicle illustrating at least one adjustable component according to another example.

Referring further to FIGS. 5-7, once the trip segments 148 have been classified based on their attributes 152, the preliminary training stage 136 can advance to step 156 of inferring a degree of fatigue that is likely to be associated with such attributes 152. The inferred degree of fatigue can be informed by a dataset stored within the vehicle-based controller 28, the remote controller(s) 120, and/or the group identity database 124. The dataset used to inform the inferred degree of fatigue can include historical data from the user pool and/or market research data for a given attribute of the trip segment(s) 148. For example, the historical data from the user pool can include geographical tags that indicate a location of the vehicle 20 when an adjustment was made to a position of the at least one adjustable component 22. This geographical tag can be used to develop correlations between positional preferences under various circumstances. The market research data can include information gleaned from user responses with regard to their experienced level of fatigue when encountering a given attribute of the trip segment(s) 148. Additionally or alternatively, the fatigue data may be determined based on the occupancy information. For example, the projected fatigue of a driver after several hours of driving through mountains may be significantly higher if the trip is done alone, as opposed to with a second passenger, or vice versa. The particular identity of the second passenger may also affect the projected fatigue of the driver.

Referring still further to FIGS. 5-7, at step 160 of the method 132, the preliminary training stage 136 can perform a training to correlate the at least one target position with the attributes 152 of the trip segments 148 and/or the inferred degree of fatigue or anxiety of the at least one occupant 26. The training performed at step 160 can employ feedback from the user and/or the group identity database 124. For example, during the training of step 160, a target position of at least one adjustable component 22 may be adjusted by the at least one controller 24, 28, 120 in response to one of the attributes 152 and/or the inferred degree of fatigue or anxiety. If, in response to the target position adjustment by the at least one controller 24, 28, 120, the at least one occupant 26 manually adjusts the at least one adjustable component 22, then the method 132 can adjust the preliminary training stage 136 to incorporate such feedback. The group identity database 124 can be updated with the same feedback. This feedback can be used to refine the method 132. The feedback, as well as the various forms of data that are discussed herein, can be tagged with identifying information for categorization within the group identity database 124. For example, such tags can include the demographic information of the at least one occupant 26, the geographic information of the at least one occupant 26, the situational information of the at least one occupant 26, and the like.

Referring again to FIGS. 5-7, once the preliminary training stage 136 has been completed, or a degree of deviation from the set-point adjusted by the vehicle-based controller 28 has decreased below a predetermined threshold, the method 132 can advance beyond the preliminary training stage 136 to step 164. At step 164, the method 132 applies collaborative filtering to match the at least one occupant 26 to an aligned cohort within the group identity database 124. For example, if the at least one occupant 26 is an adult male between the ages of eighteen and twenty-four that lives at or near a latitude that corresponds with the thirty-fifth parallel north (i.e., 35° N), then step 164 may seek to group the at least one occupant 26 with members of the user pool that have similar characteristics. With regard to collaborative filtering for a plurality of occupants, if the at least one occupant 26 includes four individuals that includes two adults and two minors (e.g., under the age of eighteen), where the four individuals live at or near a latitude that corresponds with the forty-fifth parallel north (i.e., 45° N), then the step 164 may seek to group the plurality of occupants with groups from the user pool that have similar characteristics. The foregoing examples of collaborative filtering are intended to be illustrative, not exhaustive or limiting.

As another non-limiting example, if the at least one occupant 26 is a driver that is six feet tall, then step 164 may seek to group the at least one occupant 26 with members of the user pool that have similar characteristics. If the at least one occupant 26 is a plurality of occupants including a first driver occupant that is six feet tall and a second non-driver occupant that is six feet tall positioned in a rear passenger seat directly behind the driver seat, then step 164 may seek to group the plurality of occupants with other occupancy configurations with similar characteristics.

Referring yet again to FIGS. 5-7, once the occupant 26 or group of users has been grouped with an aligned cohort from the group identity database 124, the method 132 advances to step 168 of classifying trip segments 148 along a projected travel route (predicted, planned, or current) and grouping the attributes 152 of the trip segments 148 with those categorized in the preliminary training stage 136 and/or with similar trip segment 148 attributes 152 from a personal history of the at least one occupant 26 and/or the plurality of occupants. Once the trip segments 148 have been classified and their attributes 152 evaluated, the method 132 can advance to step 172 of applying at least one target position to support an inferred preference of the at least one adjustable component 22. In inferring the preferred preference, the method 132 may reference the personal history of the at least one occupant 26 or the at least one occupant 26 and/or the plurality of occupants. Additionally or alternatively, in inferring the target position, the method 132 may reference the occupant monitoring system 128 and aggregate current fatigue or anxiety measurements of the user(s) and weight the target position options based on the current fatigue or anxiety measurements. It is contemplated that the method 132 may take into account current environmental conditions exterior to the vehicle 20 (e.g., snow, ice, rain, etc.) in determining the preferred target position. For example, when the current environmental conditions exterior to the vehicle 20 include snow and/or ice, the method 132 may prioritize a higher vehicle seat 22a position for the driver, as well as a rear-view mirror 22b position and a side mirror 22c position commensurate with an estimated position of the driver's eyes 200. When the group of users is present in the vehicle 20, the method 132 may aggregate the current anxiety and fatigue measurements of one or more of the individuals within the plurality of occupants and select, suggest, or infer the preferred target positions that are likely to lead to the lowest projected anxiety or projected fatigue for the entire group of users. It is contemplated that the individuals within the plurality of occupants may be given varying weights to their projected fatigue or projected anxiety. For example, a driver may be given a greater weight than the remainder of the plurality of occupants, a spouse of the driver may be given a greater weight than the remainder of the plurality of occupants, infants may be given a greater weight than the remainder of the plurality of occupants, and so on.

Figure 9:
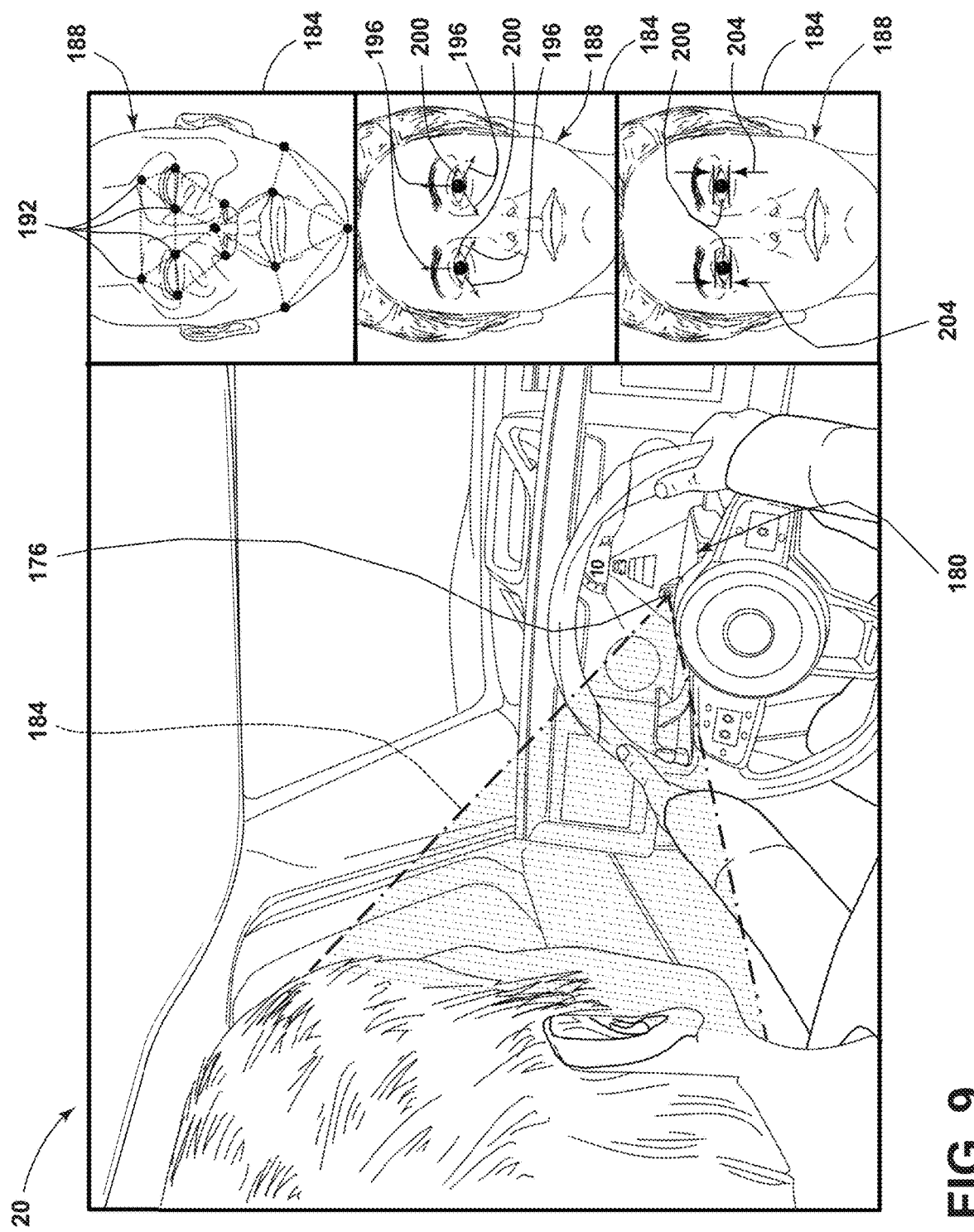
FIG. 9 is a rear perspective view of a cabin of the vehicle, illustrating a field-of-view of a cabin-facing camera according to another example.

Referring now to FIG. 9, the vehicle 20 may be provided with a cabin-facing camera 176 as part of the occupant monitoring system 128. The cabin-facing camera 176 may be positioned on a steering assembly 180 of the vehicle 20 (e.g., a steering wheel, a cabin 36 steering column shroud, etc.), on a personal mobile device of the at least one occupant 26, or any other suitable location to monitor the at least one occupant 26 (e.g., a driver occupant and/or a non-driver passenger). A field-of-view 184 of the cabin-facing camera 176 includes a face 188 of the at least one occupant 26. The occupant monitoring system 128 can identify nodal points 192 on the face 188 of the at least one occupant 26. The positioning of the nodal points 192 relative to one another, and changes thereof, can be employed in determining or inferring a current emotional state, fatigue level, and/or anxiety level of the at least one occupant 26. The occupant monitoring system 128 can also evaluate a direction of gaze 196 of eyes 200 of the at least one occupant 26. The direction of gaze 196 of the eyes 200 of the at least one occupant 26 can be used to evaluate a degree of attention of the at least one occupant 26. The occupant monitoring system 128 can further evaluate a distance 204 between eyelids of the eyes 200, which can be referred to as a degree of openness. The distance 204 between the eyelids can be employed in evaluating a degree of wakefulness of the at least one occupant 26, a current emotional state of the at least one occupant 26, a rapid change in emotional state of the at least one occupant 26, a level of fatigue of the at least one occupant 26, and/or a degree of anxiety of the at least one occupant 26. The occupant monitoring system 128 can continually monitor the at least one occupant 26 and enable the evaluation of the emotional state and/or the anxiety level, as informed by image-based emotional mapping, as a function of the attributes 152 of a given trip segment 148. For example, a convolutional neural network may be employed to analyze visual imagery collected by the occupant monitoring system 128. Such evaluation may be accomplished by the occupant monitoring system 128, the vehicle-based controller 28, the remote controller(s) 120, and/or the group identity database 124. The occupant monitoring system 128 can monitor how the at least one occupant 26 reacts to adjustments made to the at least one adjustable component 22 and enable the evaluation of how such adjustment was perceived (e.g., has fatigue level increased or decreased).

Figure 10:
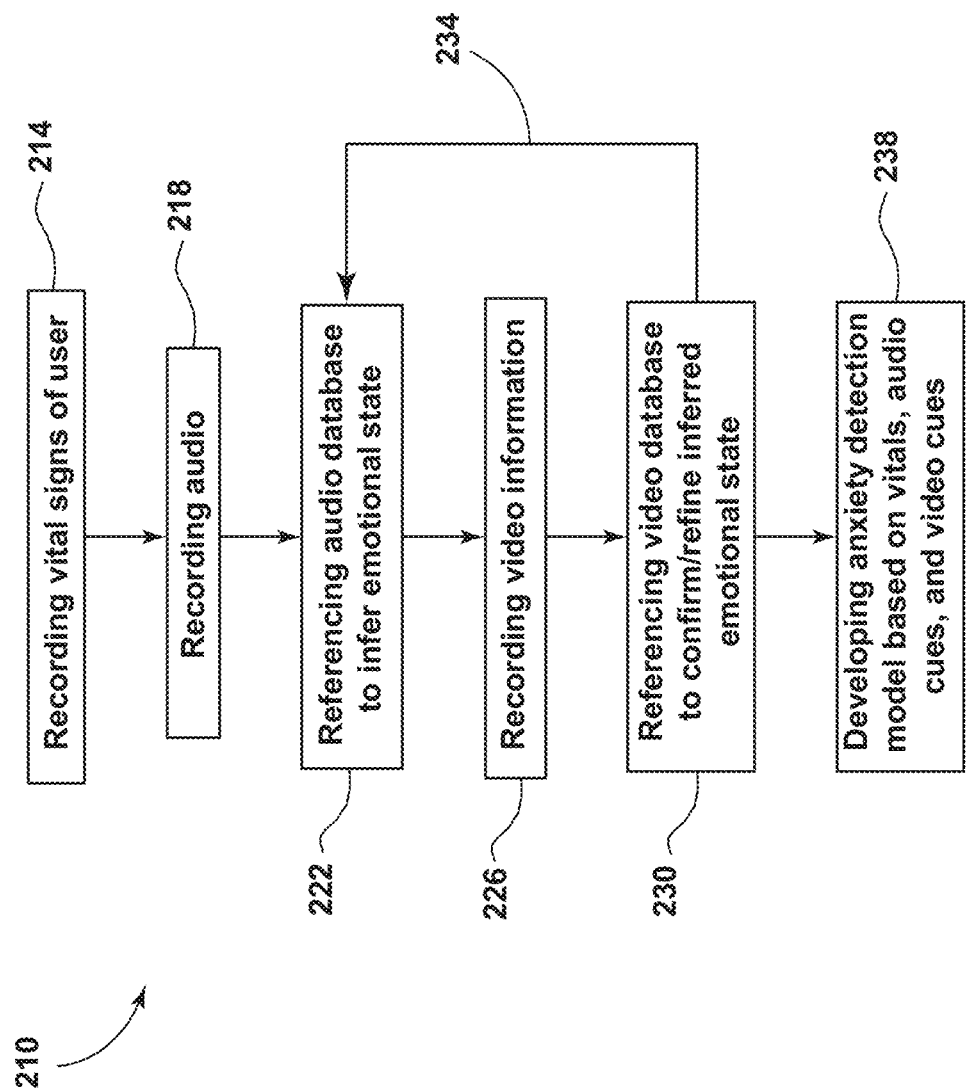
FIG. 10 is a flow diagram depicting a method for developing an anxiety detection model according to another example.

Referring to FIG. 10, a method 210 of developing an anxiety detection model is depicted in exemplary form. The anxiety detection model depicted in the method 210 can be employed in determining the inferred degree of anxiety discussed herein. The method 210 may be continually executed during operation of the vehicle 20 such that the method 210 can be refined. The method 210 includes step 214 of recording vital signs of the at least one occupant 26. The vital signs record at step 214 can include, but are not limited to, heartrate, blood pressure, respiration rate, and/or body temperature. The vital signs of the user may be collected by, for example, a heartrate monitor, a blood pressure monitor, a thermometer, a thermal imager, a camera, and/or an oxygen sensor. For example, the heartrate monitor, the blood pressure monitor, and the thermometer may be integrated into one or more wearable smart devices (e.g., smartwatch). The respiration rate may be monitored by the cabin-facing camera 176 and/or other imagers that have a field-of-view 184 that focuses on the cabin 36. In such an example, a rising and falling of the user's chest and/or shoulders can be used as an indicator of respiration rate. Additionally, or alternatively, the one or more wearable smart devices may have an oxygen sensor incorporated therein that monitors oxygen levels within a bloodstream of the user. In some examples, oxygen sensors may be positioned proximate to each of the "known" seating positions and monitored for changes in oxygen concentration within the localized environment. In such an example, a rapid decrease in oxygen concentration may be tagged as a possible increase in respiration rate for the user seated nearest. Such an event may also be compared to user entry events into the cabin 36. By performing such a comparison, it may be possible to rule out such an event as an increase in respiration rate when a user has entered and occupied a "known" seating position that was vacant in the immediate past.

Referring again to FIG. 10, the method 210 also includes step 218 of recording audio within the cabin 36. The audio recorded at step 218 is then analyzed and compared to an audio database. The audio database can be used to categorize a given audio recording with regard to an emotional state of the user from whom the audio was recorded. Accordingly, the method 210 can advance to step 222 of referencing the audio database to infer the emotional state of the user from whom the audio was recorded at step 218. The method 210 can also include step 226 of recording video information (e.g., with the cabin-facing camera 176). At step 230, the video information recorded at step 226 can be referenced against a video database in an effort to confirm and/or refine the inferred emotional state from step 222. The video database can be used to categorize a gesture and/or facial expression using image-based emotional mapping, as discussed above. The process outlined with regard to steps 222, 226, and 230 can be repeated in an iterative manner, as indicated by arrow 234. The method 210 may conclude with step 238 of developing an anxiety detection model based on the vital signs, audio cues, and video cues of a user of the vehicle 20. The developed anxiety detection model can be employed for the inferred degree of anxiety discussed herein.

Figure 11:
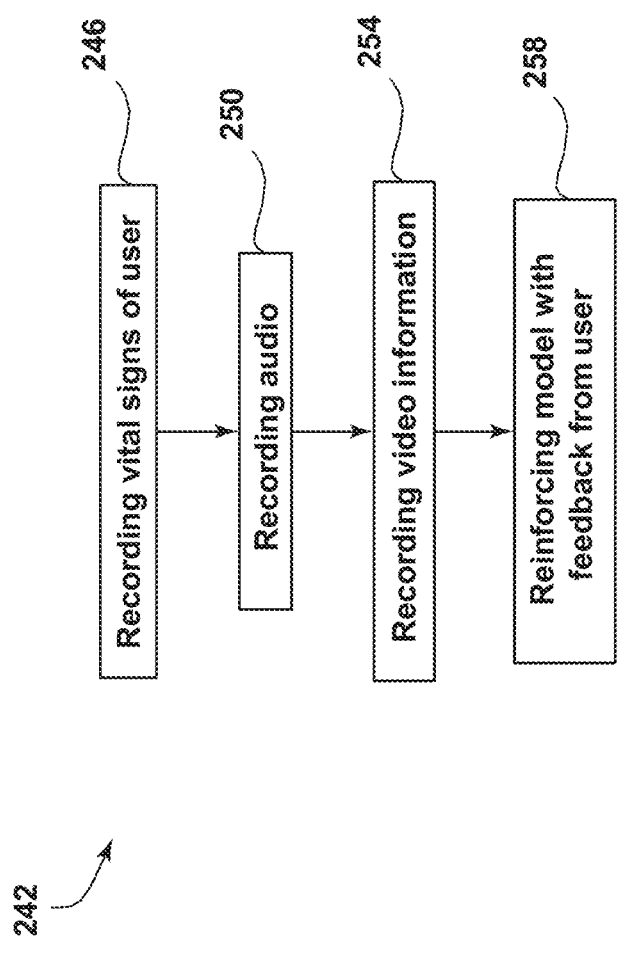
FIG. 11 is a flow diagram depicting a method for inferring a degree of anxiety of a user according to another example.
Figure 12:
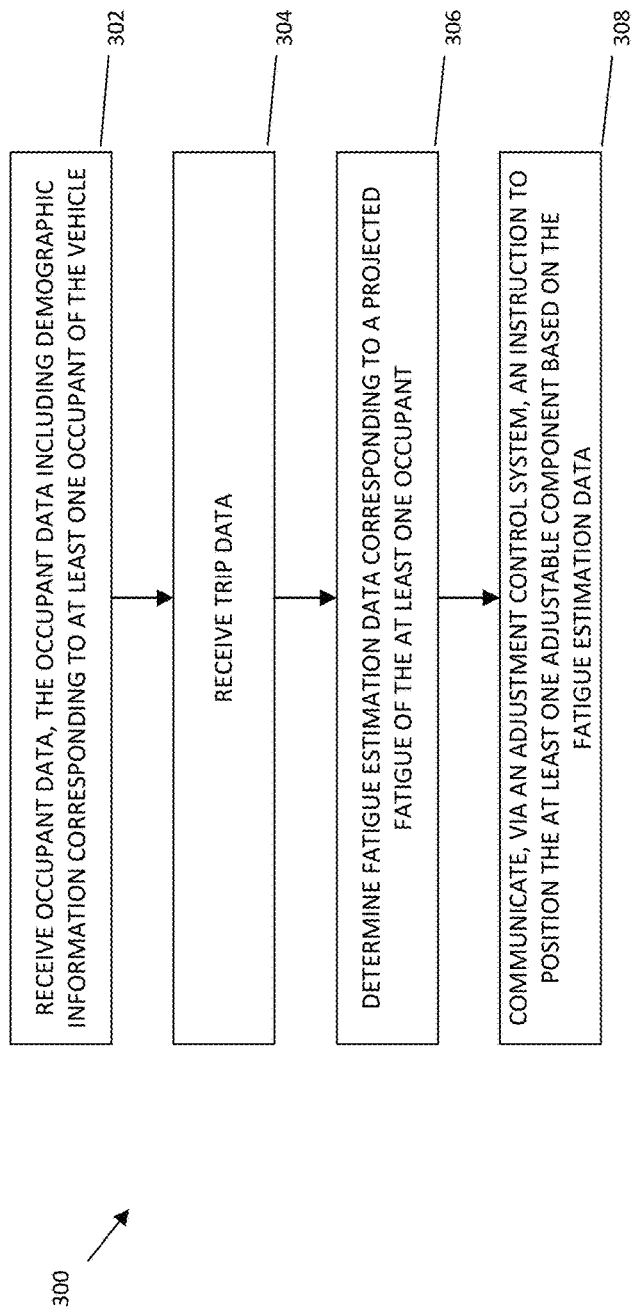
FIG. 12 is a flow diagram depicting a method for controlling at least one adjustable component of the vehicle according to another example.

Referring now to FIG. 11, a method 242 of inferring a degree of anxiety of a user is depicted in exemplary form. The method 242 can employ the developed anxiety detection model discussed with regard to method 210 in FIG. 9. The method 242 includes step 246 of recording the vital signs of the user. The method 242 also includes step 250 of recording audio within the cabin 36. The method 242 further includes step 254 of recording video information. Several parallels exist between method 210 and method 242. A distinction between methods 210 and 242 can be drawn with regard to developing a model versus applying and/or refining the model. In method 242, step 258 reinforces the developed anxiety detection model that was developed in method 210. At step 258, the reinforcement of the developed anxiety detection model is provided in the form of feedback from the user. For example, the user may be asked to rate their current degree of anxiety. This user-provided data can be used to inform the refinement of the method 210 and/or the method 242. Similarly, the user may be asked if they would characterize their current emotional state as a particular emotion. That is, the feedback provided by the user may be qualitative and/or quantitative.

Referring to FIGS. 12-15, a method 300 for controlling at least one adjustable component 22 of a vehicle 20 is depicted in exemplary form. In some examples, the at least one adjustable component 22 of the vehicle 20 includes at least one of the vehicle seat 22a, the vehicle mirrors 22b, 22c, the steering component 22d, and the pedal assembly 22e. The method 300 includes step 302 of receiving occupant data. In some examples, the occupant data includes demographic information corresponding to at least one occupant 26 of the vehicle 20. The method 300 includes step 304 of receiving trip data. In some examples, the trip data includes travel route information and occupancy information. In some examples, the travel route information corresponds to a projected travel route and the occupancy information corresponds to at least one of a number of occupants, an identity of the at least one occupant 26, and a position of the at least one occupant 26. The method 300 includes step 306 of determining fatigue estimation data corresponding to a projected fatigue of the at least one occupant 26 along the projected travel route based on the trip data. In some examples, the fatigue estimation data includes target position data corresponding to at least one target position for the at least one adjustable component 22. The method 300 includes step 308 of communicating, via an adjustment control system 24, an instruction to position the at least one adjustable component 22 based on the fatigue estimation data. It is contemplated that, in some examples, step 302, step 304, and/or step 306 can be executed on one or more of the one or more remote controllers 120. In such an example, the instructions communicated at step 308 can be received by the vehicle-based controller 28. The method 300 can also include adjusting the at least one adjustable component 22. By way of example, the adjustment control system 24 may be operable to adjust the at least one adjustable component 22 via the at least one positioning actuator 30.

Figure 13:
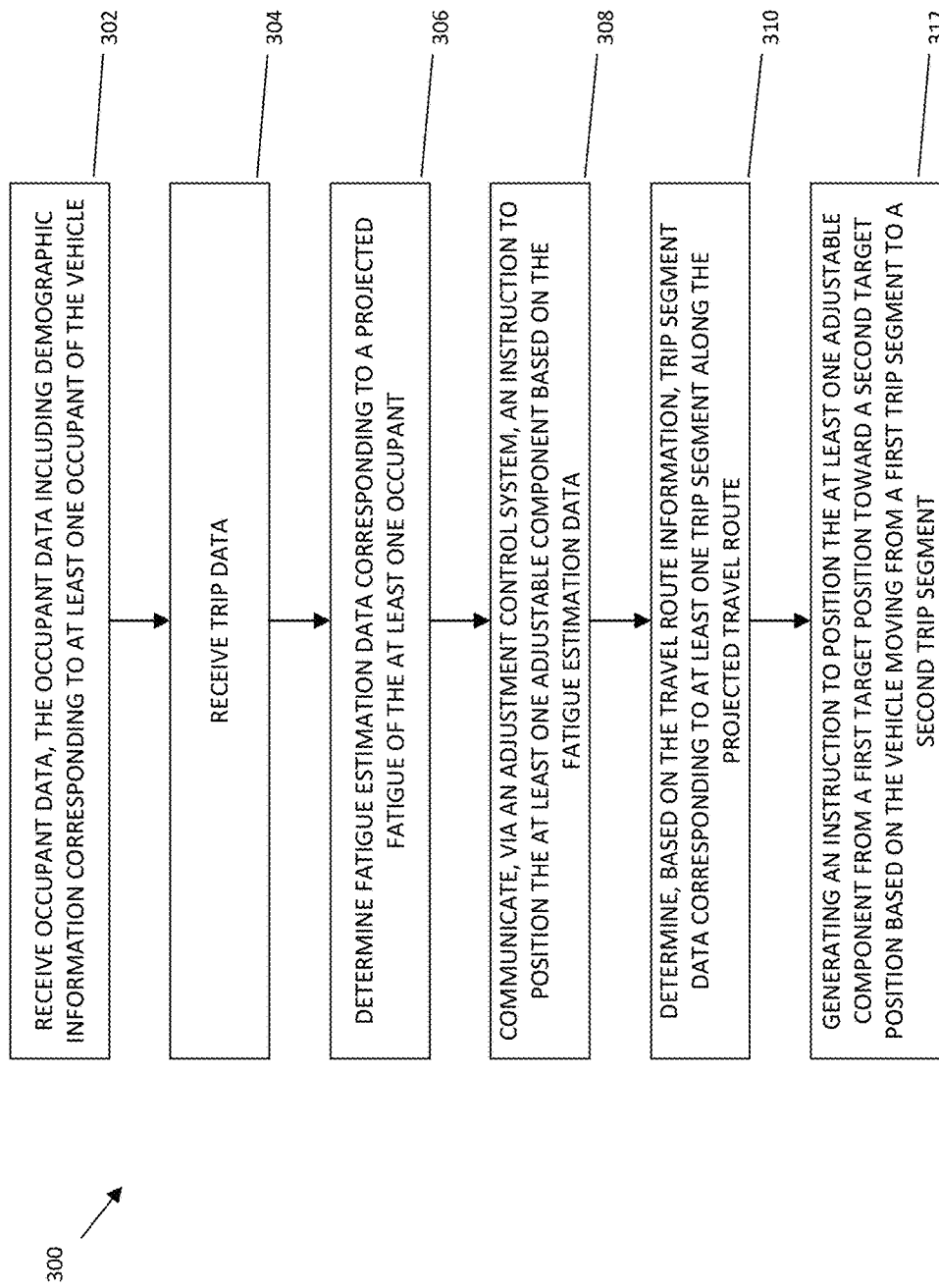
FIG. 13 is a flow diagram depicting a method for controlling at least one adjustable component of the vehicle according to another example.

Referring to FIG. 13, the method 300 may include determining, based on the travel route information, trip segment data corresponding to the at least one trip segment 148 along the projected travel route. In some examples, the at least one trip segment 148 includes at least one travel segment profile metric having at least one of road type information, geographical information, topographical information, traffic density information, departure time information, arrival time information, and regulatory information (e.g., a speed limit). In some examples, the at least one target position includes a plurality of target positions and the at least one trip segment 148 includes a plurality of trip segments 148. The plurality of target positions can correspond to the plurality of trip segments 148. The method 300 can include the step 312 of generating, via the adjustment control system 24, an instruction to position the at least one adjustable component 22 from a first target position of the plurality of target positions toward a second target position of the plurality of target positions based on the vehicle 20 moving from a first trip segment of the plurality of trip segments 148 to a second trip segment of the plurality of trip segments 148. For example, the first target position may be a reclined position of the vehicle seat 22a corresponding to rural highway driving, and the second target position may refer to an upright position of the vehicle seat 22a corresponding to high-traffic city driving.

Figure 14:
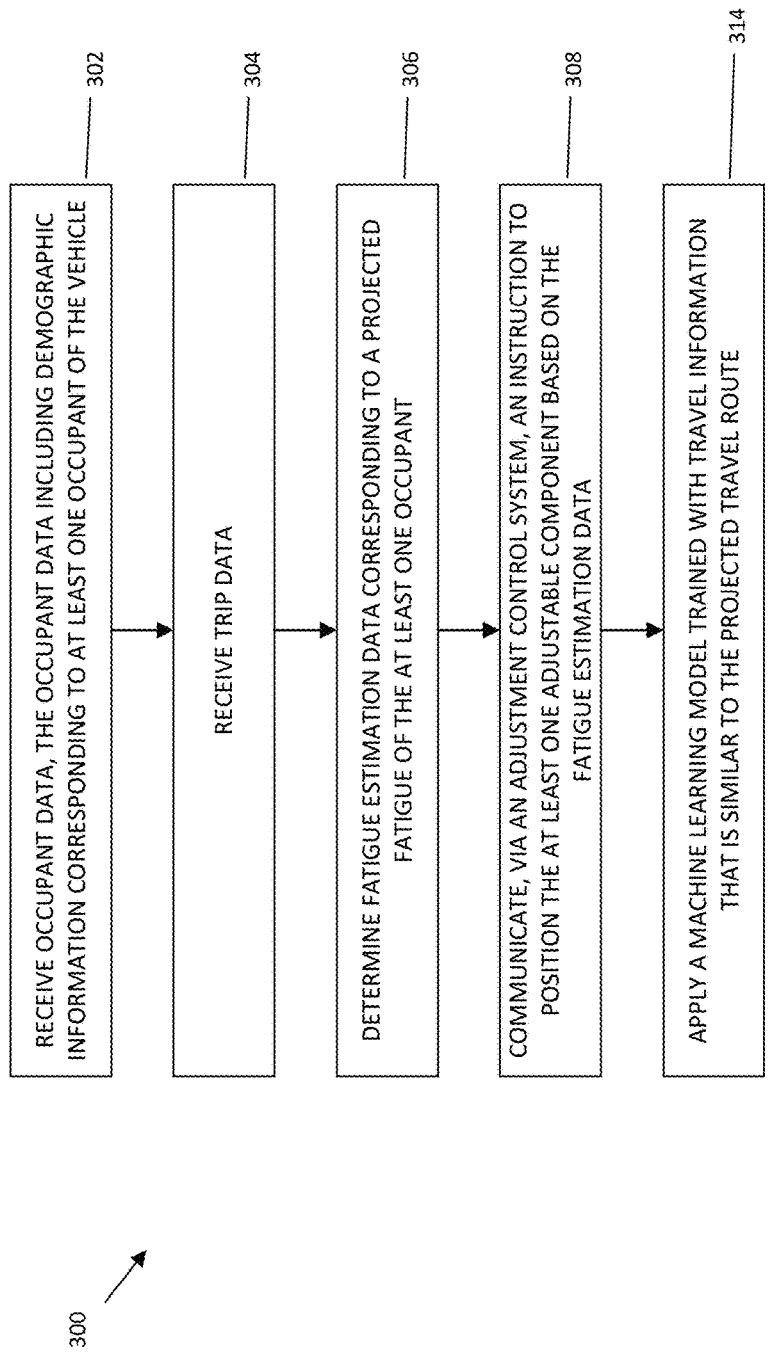
FIG. 14 is a flow diagram depicting a method for controlling at least one adjustable component of the vehicle according to another example.

Referring to FIG. 14, the method 300 can include step 314 of applying a machine learning model trained with travel route information that is similar to the projected travel route. In some examples, the fatigue estimation data is determined via access to a group identity database 124 that includes a plurality of group identity profiles. In some examples, the method 300 may be performed via one or more of the controllers 24, 28, 120 (e.g., with some tasks performed by controller 24, other tasks performed by controller 28, and still other tasks performed by controller 120). For example, the at least one controller 24, 28, 120 may include a controller on a personal mobile device of the at least one occupant 26 and a local controller of the vehicle 20. In some examples, the at least one controller 24, 28, 120 communicates the occupant data and the trip data to the group identity database 124. The at least one controller 24, 28, 120 may further receive the target position data from the group identity database 124 and may be determined based on the occupant data and the trip data.

Figure 15:
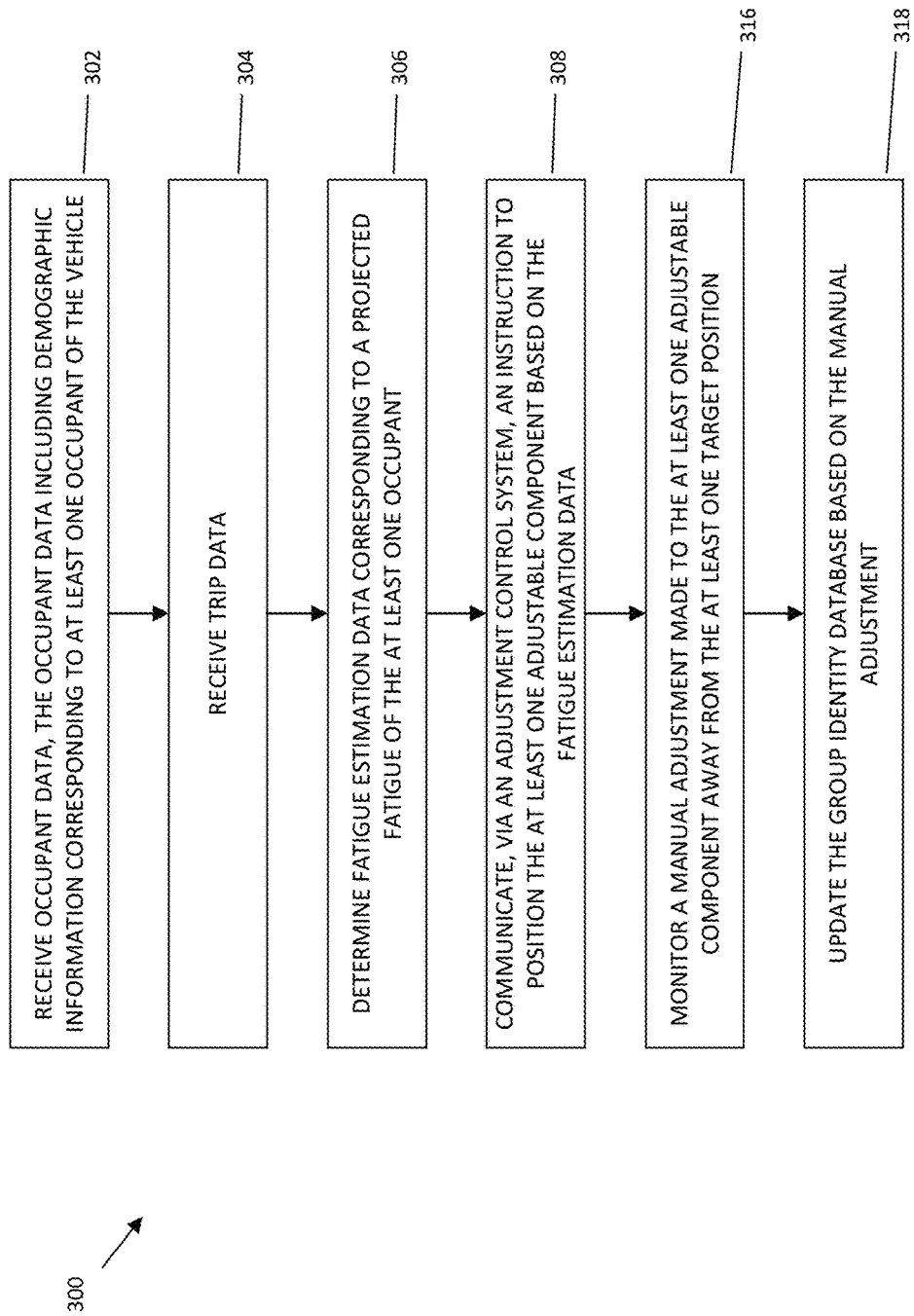
FIG. 15 is a flow diagram depicting a method for controlling at least one adjustable component of the vehicle according to another example.
Figure 16:
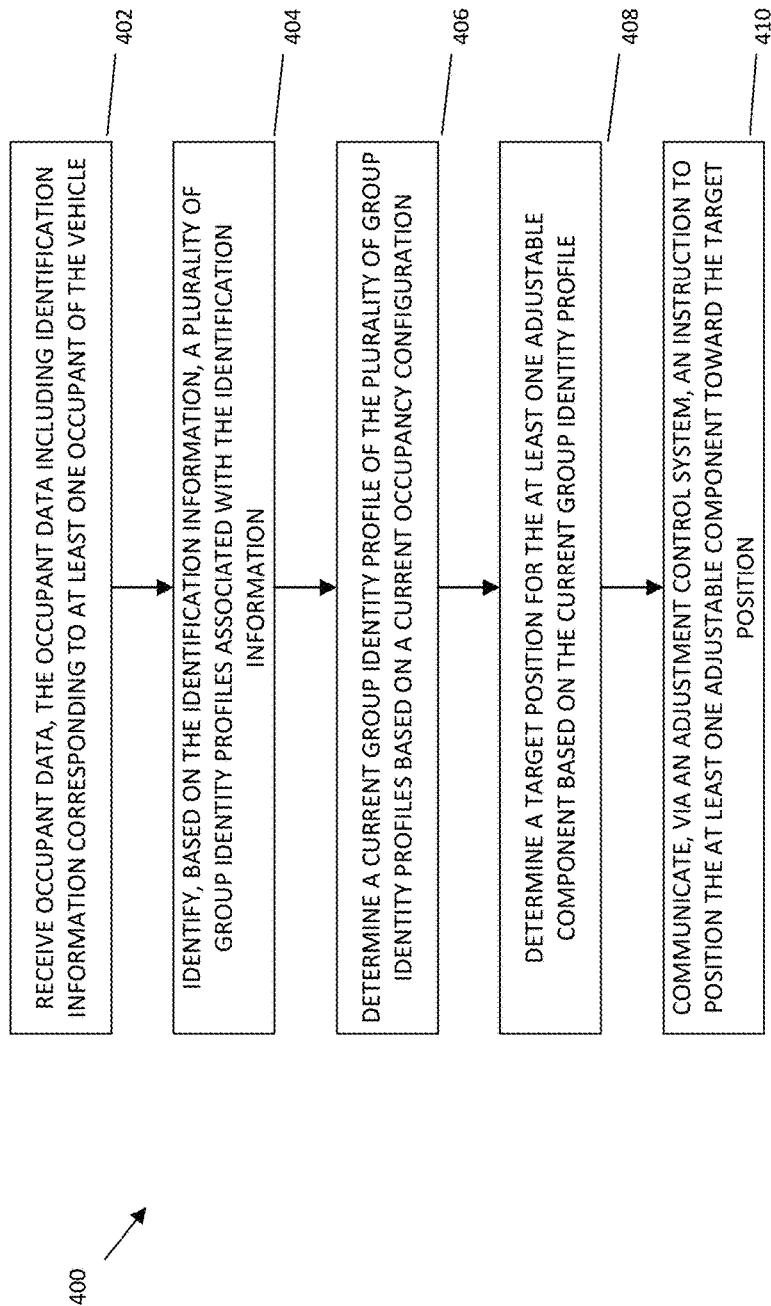
FIG. 16 is a flow diagram depicting a method for controlling at least one adjustable component of the vehicle according to another example.

Referring to FIG. 15, the method 300 can include step 316 of monitoring a manual adjustment made to the at least one adjustable component 22 away from the at least one target position. The method 300 can include the step 318 of updating the group identity database 124 based on the manual adjustment to the at least one adjustable component 22. It is generally contemplated that steps 302-318, and/or sub-processes within steps 302-318, can be accomplished and/or improved upon via the at least one controller 24, 28, 120. For example, the at least one controller 24, 28, 120 may receive the occupant data, receive the trip data, determine the fatigue estimation data, and may operate in tandem with the adjustment control system 24 to communicate the instruction to position the at least one adjustable component 22 based on the fatigue estimation data. Further, the at least one controller 24, 28, 120 may determine the trip segment data and generate the instruction to position the at least one component toward the second target position based on the vehicle 20 moving from the first trip segment to the second trip segment. In addition, the at least one controller 24, 28, 120 may apply the machine learning model. Additionally, or alternatively, the at least one controller 24, 28, 120 may monitor the manual adjustment and update the group identity database 124 based on the manual adjustment.

Figure 17:
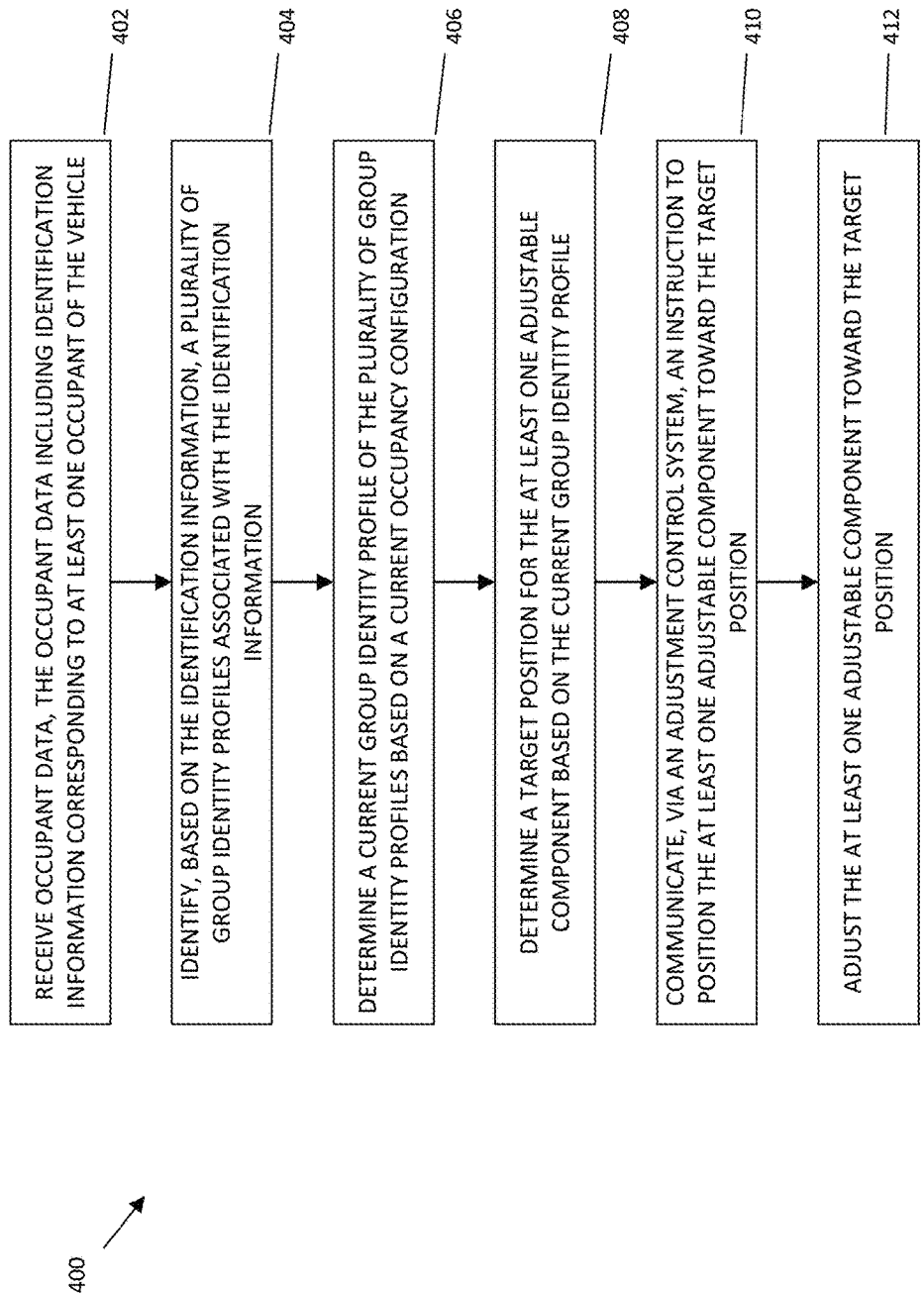
FIG. 17 is a flow diagram depicting a method for controlling at least one adjustable component of the vehicle according to another example.

Referring to FIGS. 16-20, a method 400 for controlling at least one adjustable component 22 of a vehicle 20 is exemplarily shown. In some examples, the at least one adjustable component 22 of the vehicle 20 includes at least one of the vehicle seat 22a, the vehicle mirrors 22b, 22c, the steering component 22d, and the pedal assembly 22e. The method 400 includes step 402 of receiving occupant data. In some examples, the occupant data includes identification information corresponding to the at least one occupant 26 of the vehicle 20. The method 400 includes step 404 of identifying, based on the identification information, a plurality of group identity profiles associated with the identification information. In some examples, each of the plurality of group identity profiles corresponds to one of a plurality of occupancy configurations. The method 400 includes step 406 of determining a current group identity profile of the plurality of group identity profiles based on a current occupancy configuration of the plurality of occupancy configurations. In some examples, each of the plurality of group identity profiles includes occupancy information corresponding to a number of occupants in the vehicle 20 and an identity of the at least one occupant 26 of the vehicle 20. Step 406 may include referencing a group identity database 124. The group identity database 124 may include the plurality of group identity profiles. The method 400 includes step 408 of determining a target position for the at least one adjustable component 22 based on the current group identity profile. The method 400 includes step 410 of communicating, via an adjustment control system 24, an instruction to position the at least one adjustable component 22 toward the target position. Referring to FIG. 17, the method 400 can include step 412 of adjusting the at least one adjustable component 22 toward the target position.

Figure 18:
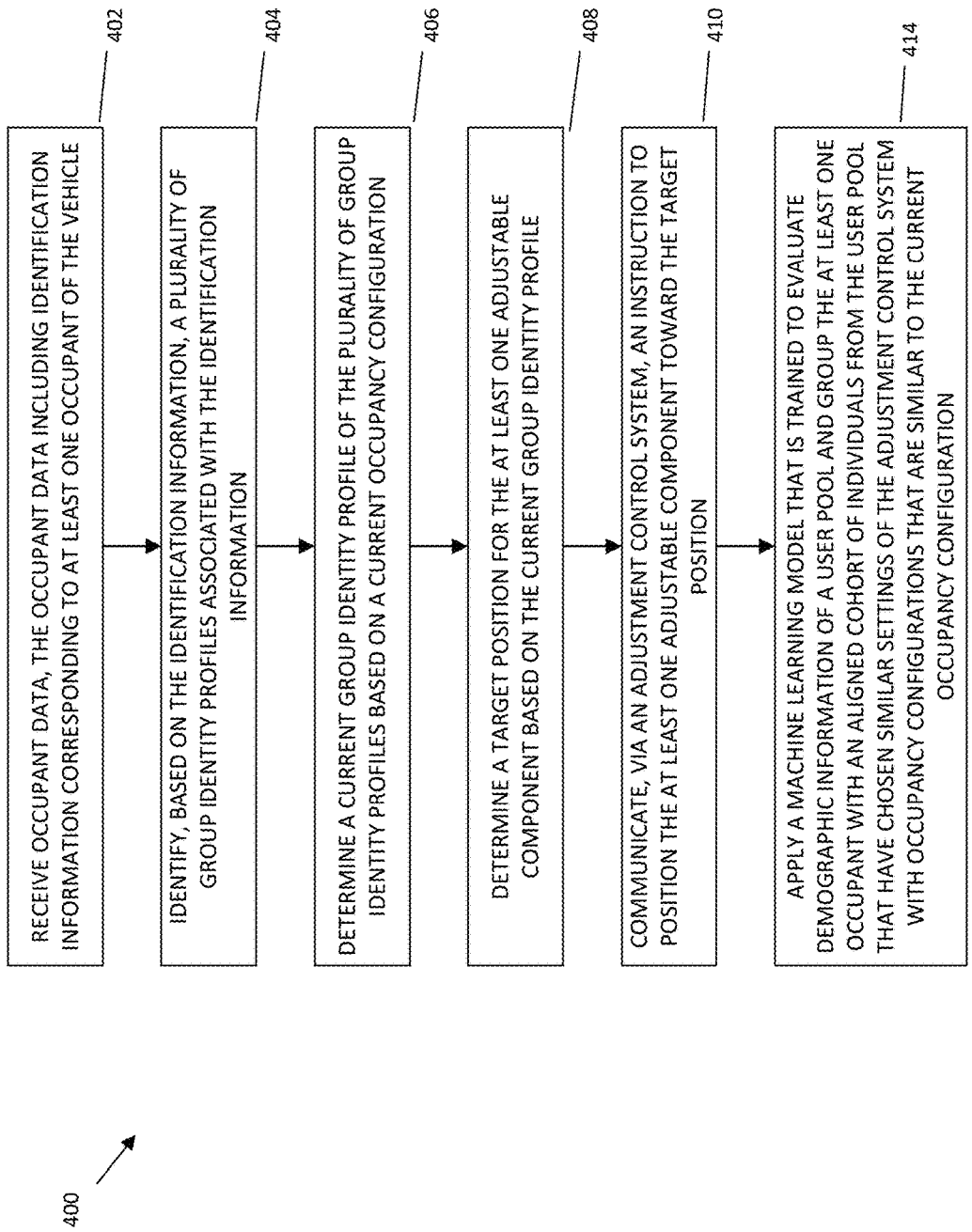
FIG. 18 is a flow diagram depicting a method for controlling at least one adjustable component of the vehicle according to another example.
Figure 19:
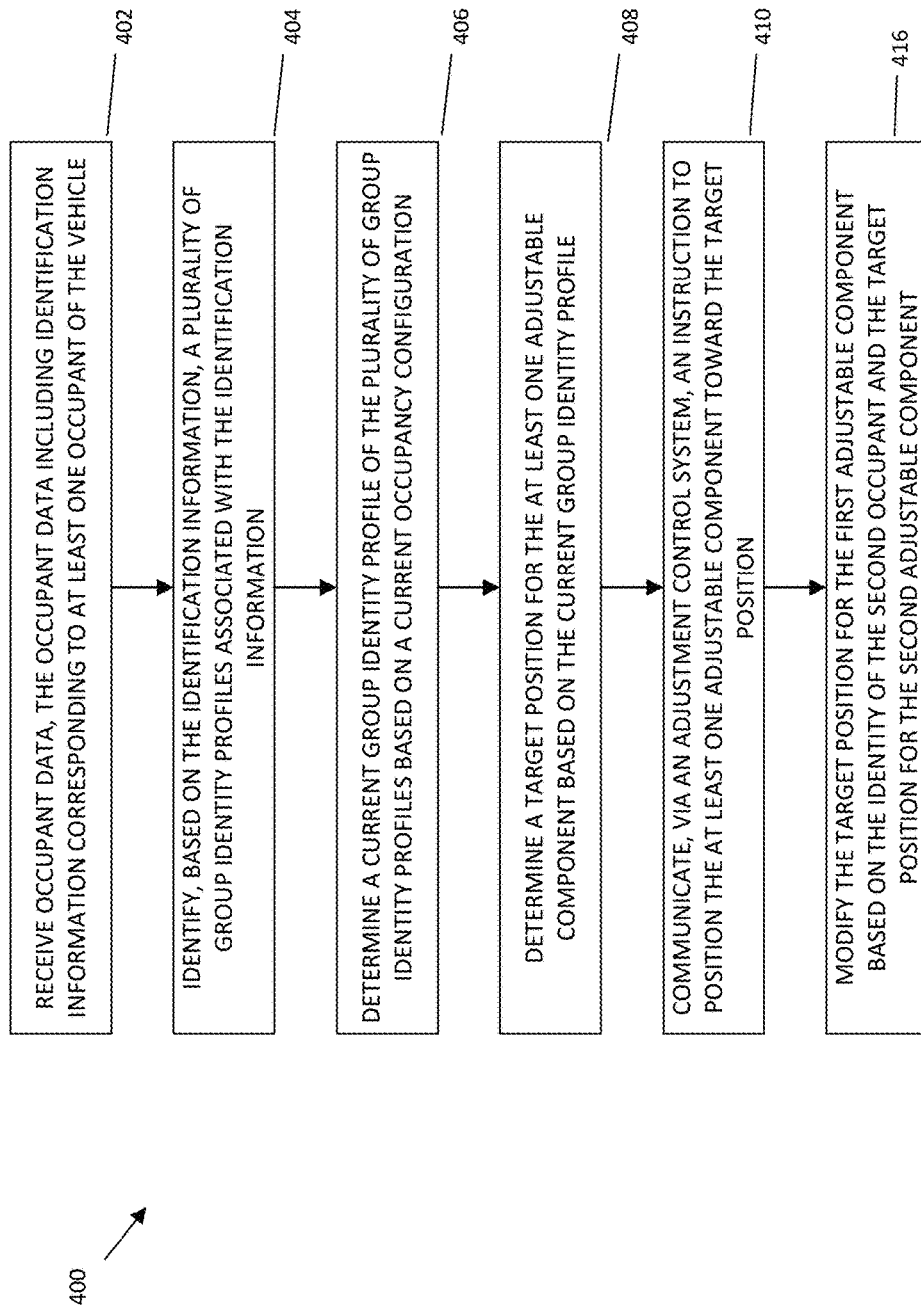
FIG. 19 is a flow diagram depicting a method for controlling at least one adjustable component of the vehicle according to another example.

Referring to FIG. 18, the method 400 can include step 414 of applying a machine learning model that is trained to evaluate demographic information of a user pool and group the at least one occupant 26 with an aligned cohort of individuals from the user pool that have chosen similar settings of the adjustment control system 24 with occupancy configurations that are similar to the current occupancy configuration. In some examples, the at least one occupant 26 can include a first occupant and a second occupant. The identification information can include an identity of the first occupant and an identity of the second occupant. The at least one adjustable component 22 can include a first adjustable component associated with the first occupant and a second adjustable component associated with a second occupant. Referring to FIG. 19, the method 400 can include step 416 of modifying the target position for the first adjustable component based on the identity of the second occupant and the target position for the second adjustable component. In some examples, the first adjustable component is a vehicle seat 22a of the driver of the vehicle 20, and the second adjustable component is a vehicle seat 22a of a non-driver passenger of the vehicle 20.

Figure 20:
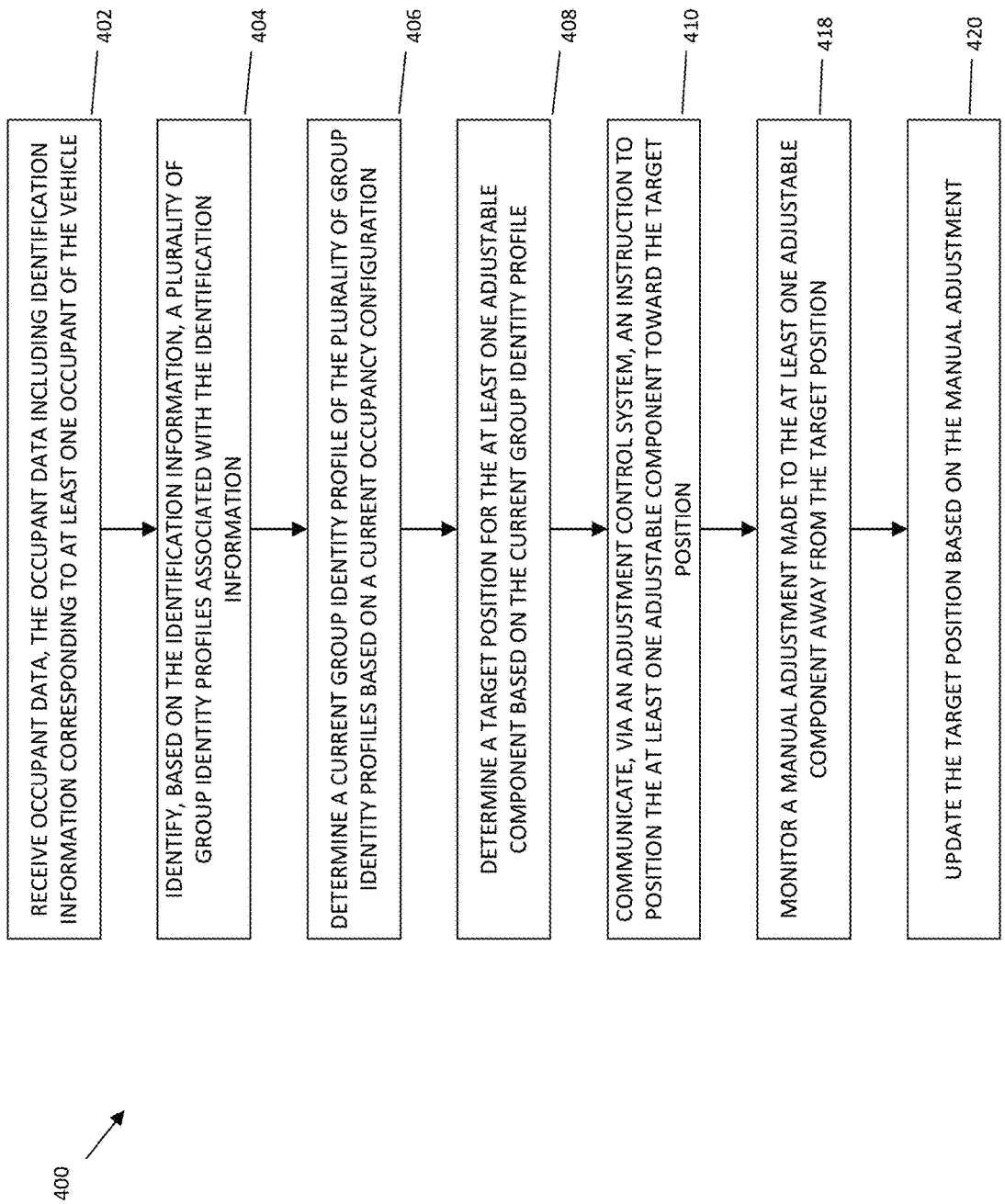
FIG. 20 is a flow diagram depicting a method for controlling at least one adjustable component of the vehicle according to another example.

Referring to FIG. 20, the method 400 can include step 418 of monitoring a manual adjustment made to the at least one adjustable component 22 away from the target position. The method 400 can include step 420 of updating the target position based on the manual adjustment. In some examples, an occupancy detection system 34 determines the current occupancy configuration of the vehicle 20. In some examples, the method 400 may be performed via one or more of the controllers 24, 28, 120 (e.g., with some tasks performed by controller 24, other tasks performed by controller 28, and still other tasks performed by controller 120). For example, the at least one controller 24, 28, 120 may include a controller on a personal mobile device of the at least one occupant 26 and a local controller of the vehicle 20. In some examples, the at least one controller 24, 28, 120 communicates the occupant data and the trip data to the group identity database 124. The at least one controller 24, 28, 120 may further receive the target position data from the group identity database 124 and may be determined based on the occupant data and the trip data. The at least one controller 24, 28, 120 may determine the target position for the at least one adjustable component 22 based on the current group identity profile. It is generally contemplated that steps 402-420, and/or sub-processes within steps 402-420, can be accomplished and/or improved upon via the at least one controller 24, 28, 120. For example, the at least one controller 24, 28, 120 may receive the occupant data, identify the plurality of group identity profiles, determine the current group identity profile, and determine the target position, and operate in tandem with the adjustment control system 24 to communicate the instruction. In addition, the at least one controller 24, 28, 120 may apply the machine learning model. Additionally, or alternatively, the at least one controller 24, 28, 120 may modify the target position. The at least one controller 24, 28, 120 may further update the target position.

In some examples, the group identity database 124 applies a machine learning model that is trained to predict the current group identity profile that corresponds to the current occupancy configuration. In some examples, the machine learning model is further trained to determine anxiety data corresponding to a projected anxiety of the at least one occupant 26 based on the current group configuration, wherein determining the target position data is further based on the anxiety data.

Figure 21:
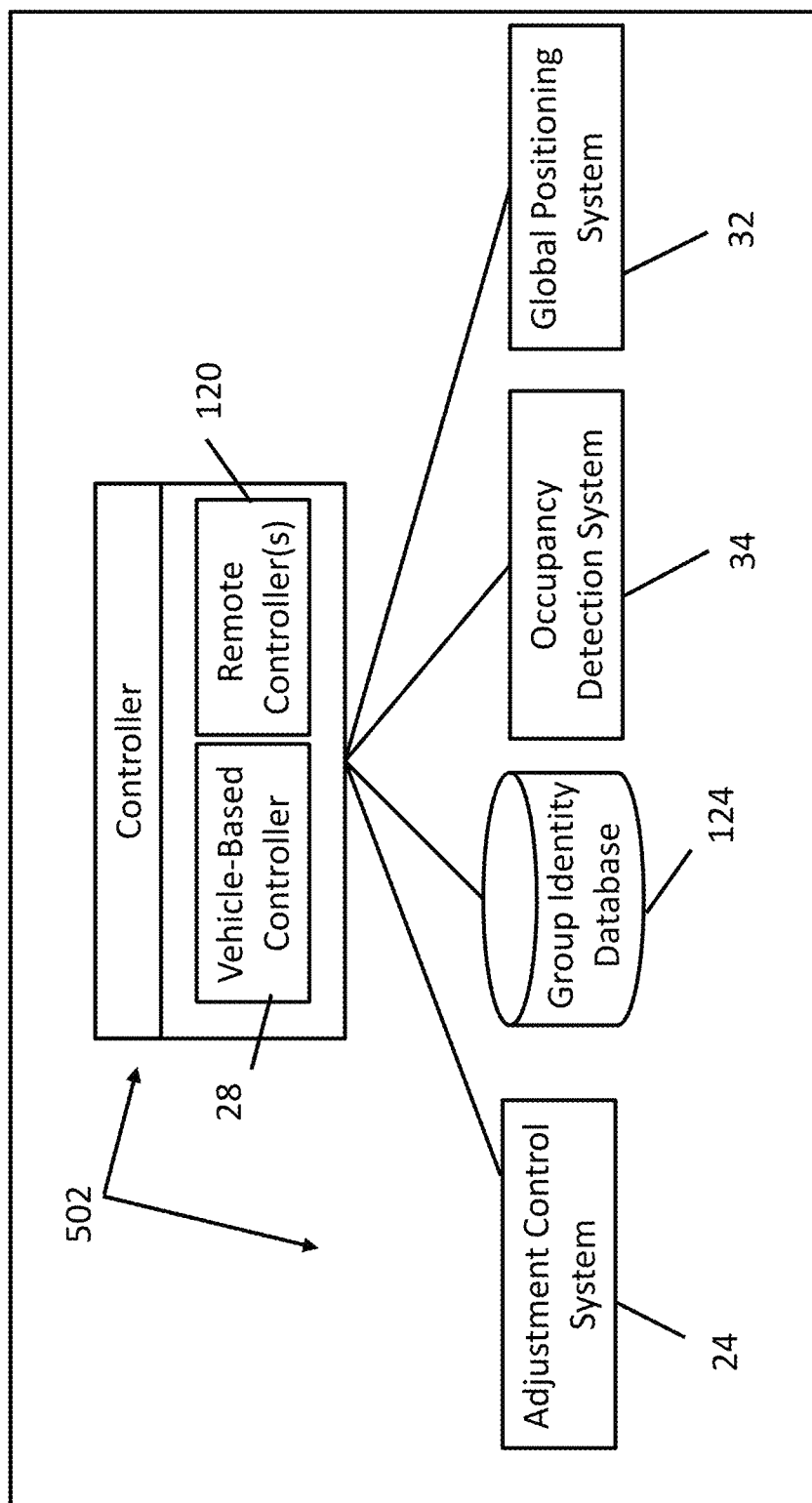
FIG. 21 is a block diagram of a system for controlling at least one adjustable component of the vehicle according to another example.

Referring now to FIG. 21, a system 500 for adjusting an adjustable component 22 of the vehicle 20 is depicted in exemplary form. The system 500 includes the adjustment control system 24. The adjustment control system 24 can adjust the at least one adjustable component 22. The system 500 also includes the Global Positioning System (GPS) 32. The Global Positioning System (GPS) 32 provides geographic information (e.g., to the vehicle-based controller 28 and/or one or more of the one or more remote controllers 120). The system 500 further includes the group identity database 124. The system 500 also includes the occupancy detection system 34 that determines a current occupancy configuration of the vehicle 20. Additionally, the system 500 includes at least one controller 502. The at least one controller 388 can include, but is not limited to, the vehicle-based controller 28, the adjustment control system 24, and/or one or more of the one or more remote controllers 120.

Referring again to FIG. 21, the at least one controller 502 receives the occupant data. The at least one controller 502 receives the trip data. The at least one controller 502 determines fatigue estimation data corresponding to a projected fatigue of the at least one occupant 26 along the projected travel route based on the trip data. The at least one controller 502 communicates, via the adjustment control system 24, an instruction to position the at least one adjustable component 22 based on the fatigue estimation data. The at least one controller 502 can generate, via the adjustment control system 24, an instruction to position the at least one adjustable component 22 from a first target position of the plurality of target positions toward a second target position of the plurality of target positions based on the vehicle 20 moving from a first trip segment of the plurality of trip segments 148 to a second trip segment of the plurality of trip segments 148. The at least one controller 502 can monitor a manual adjustment made to the at least one adjustable component 22 away from the at least one target position. The at least one controller 502 can update the group identity database 124 based on the manual adjustment.

The at least one controller 502 can receive occupant data, the occupant data including identification information corresponding to at least one occupant 26 of the vehicle 20. The at least one controller 502 can identify, based on the identification information, a plurality of group identity profiles associated with the identification information. The at least one controller 502 can determine a current group identity profile of the plurality of group identity profiles based on the current occupancy configuration of the plurality of occupancy configurations. The at least one controller 502 can reference the group identity database 124. The at least one controller 502 can determine a target position for the at least one adjustable component 22 based on the current group identity profile. The at least one controller 502 can communicate, via the adjustment control system 24, an instruction to position the at least one adjustable component 22 toward the target position. The at least one controller 502 can adjust the at least one adjustable component 22 toward the target position. The at least one controller 502 can apply a machine learning model that is trained to evaluate demographic information of a user pool and group the at least one occupant 26 with an aligned cohort of individuals from the user pool that have chosen similar settings of the adjustment control system 24 with occupancy configurations that are similar to the current occupancy configuration. The at least one controller 502 can also monitor a manual adjustment made to the at least one adjustable component 22 away from the target position and update the target position based on the manual adjustment. The at least one controller 502 can also determine anxiety data corresponding to a projected anxiety of the at least one occupant 26 based on the current group configuration. The at least one controller 502 may determine the target position based on the anxiety data.

It is generally contemplated that a system for controlling at least one adjustable component 22 of a vehicle 20 includes a group identity database 124 that applies a machine learning model trained to predict a current group identity profile corresponding to a current occupancy configuration. In some examples, the current group identity profile includes occupancy information corresponding to a number of occupants in the vehicle 20 and an identity of at least one occupant 26 of the vehicle 20. The current group identity profile can be predicted based on another group identity profile having at least one characteristic similar to the occupancy data. The machine learning model is also trained to determine, based on the current group identity profile, target position data corresponding to a target position for the at least one adjustable component 22. The system also includes at least one controller 24, 28, 120 that receives, from the group identity database 124, the target position data for the at least one adjustable component 22. The at least one controller 24, 28, 120 also communicates, via an adjustment control system 24, an instruction to position the at least one adjustable component 22 toward the target position based on the target position data. The machine learning model can also be trained to determine anxiety data corresponding to a projected anxiety of the at least one occupant 26 based on the occupancy information. Determining the target position data may be further based on the anxiety data.

Modifications of the disclosure will occur to those skilled in the art and to those who make or use the concepts disclosed herein. Therefore, it is understood that the embodiments shown in the drawings and described above are merely for illustrative purposes and not intended to limit the scope of the disclosure, which is defined by the following claims as interpreted according to the principles of patent law, including the doctrine of equivalents.

It will be understood by one having ordinary skill in the art that construction of the described concepts, and other components, is not limited to any specific material. Other exemplary embodiments of the concepts disclosed herein may be formed from a wide variety of materials, unless described otherwise herein.

For purposes of this disclosure, the term "coupled" (in all of its forms: couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature, or may be removable or releasable in nature, unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, and the nature or numeral of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes, or steps within described processes, may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further, it is to be understood that such concepts are intended to be covered by the following claims, unless these claims, by their language, expressly state otherwise.

What is claimed is:

1. A method for controlling at least one adjustable component of a vehicle, the method comprising:
   receiving occupant data via at least one controller, the occupant data including demographic information corresponding to at least one occupant of the vehicle;

receiving trip data via the at least one controller, the trip data including travel route information and occupancy information, wherein the travel route information corresponds to a projected travel route and the occupancy information corresponds to at least one of a number of occupants, an identity of the at least one occupant, and a position of the at least one occupant;

determining, via the at least one controller, fatigue estimation data corresponding to a projected fatigue of the at least one occupant along the projected travel route based on the trip data, wherein the fatigue estimation data is determined via access to a group identity database that includes a plurality of group identity profiles associated with identification information of the at least one occupant;

determining a current group identity profile of the plurality of group identity profiles based on the occupancy information;

communicating, via an adjustment control system, an instruction to position the at least one adjustable component based on the fatigue estimation data and the current group identity profile; and adjusting the at least one adjustable component toward at least one target position.

2. The method for controlling at least one adjustable component of a vehicle of claim 1, wherein the at least one adjustable component includes at least one of a vehicle seat, a vehicle mirror, a steering component, and a pedal assembly.

3. The method for controlling at least one adjustable component of a vehicle of claim 1, further comprising:

determining, based on the travel route information, trip segment data corresponding to at least one trip segment along the projected travel route via the at least one controller, wherein the at least one trip segment includes at least one travel segment profile metric having at least one of road type information, geographical information, topographical information, traffic density information, departure time information, arrival time information, and regulatory information.

4. The method for controlling at least one adjustable component of a vehicle of claim 3, wherein the at least one target position is a plurality of target positions and the at least one trip segment is a plurality of trip segments, and wherein the plurality of target positions corresponds to the plurality of trip segments.

5. The method for controlling at least one adjustable component of a vehicle of claim 4, further comprising:

generating, via the adjustment control system, an instruction to position the at least one adjustable component from a first target position of the plurality of target positions toward a second target position of the plurality of target positions based on the vehicle moving from a first trip segment of the plurality of trip segments to a second trip segment of the plurality of trip segments.

6. The method for controlling at least one adjustable component of a vehicle of claim 1, wherein the method further includes:

applying a machine learning model trained with stored travel route information that is similar to the projected travel route to the projected travel route to generate the instruction to position the at least one adjustable component.

7. The method for controlling at least one adjustable component of a vehicle of claim 1, further comprising:

monitoring a manual adjustment made to the at least one adjustable component away from the at least one target position via the at least one controller; and updating, via the at least one controller, the group identity database based on the manual adjustment.

8. A system for controlling at least one adjustable component of a vehicle, the system comprising:

at least one positioning actuator that adjusts the at least one adjustable component;

an adjustment control system that controls the at least one positioning actuator; and at least one controller:

that receives occupant data, the occupant data including demographic information corresponding to at least one occupant of the vehicle;

that receives trip data, the trip data including travel route information and occupancy information, wherein the travel route information corresponds to a projected travel route and the occupancy information corresponds to at least one of a number of occupants, an identity of the at least one occupant, and a position of the at least one occupant;

that determines fatigue estimation data corresponding to a projected fatigue of the at least one occupant along the projected travel route based on the trip data, wherein the fatigue estimation data is determined via access to a group identity database that includes a plurality of group identity profiles associated with identification information of the at least one occupant;

that determines a current group identity profile of the plurality of group identity profiles based on the occupancy information; and that communicates, via the adjustment control system, an instruction to position the at least one adjustable component based on the fatigue estimation data and the current group identity profile.

9. The system for controlling at least one adjustable component of a vehicle of claim 8, wherein the at least one controller further controls the at least one adjustable component to adjust the at least one adjustable component toward at least one target position.

10. The system for controlling at least one adjustable component of a vehicle of claim 9, wherein the at least one adjustable component includes at least one of a vehicle seat, a vehicle mirror, a steering component, and a pedal assembly.

11. The system for controlling at least one adjustable component of a vehicle of claim 9, wherein the at least one controller comprises a controller on a personal mobile device of the at least one occupant and a local controller of the vehicle.

12. The system for controlling at least one adjustable component of a vehicle of claim 9, further comprising:

trip segment data corresponding to at least one trip segment along the projected travel route, wherein the at least one target position is a plurality of target positions and the at least one trip segment is a plurality of trip segments, and wherein the plurality of target positions corresponds to the plurality of trip segments.

13. The system for controlling at least one adjustable component of a vehicle of claim 12, wherein the adjustment control system generates an instruction to position the at least one adjustable component from a first target position of the plurality of target positions toward a second target position of the plurality of target positions based on the vehicle moving from a first trip segment of the plurality of trip segments to a second trip segment of the plurality of trip segments.

14. The system for controlling at least one adjustable component of a vehicle of claim 8, wherein the at least one controller applies a machine learning model with stored travel route information that is similar to the projected travel route.

15. The system for controlling at least one adjustable component of a vehicle of claim 14, wherein the at least one controller:
monitors a manual adjustment made to the at least one adjustable component away from the at least one target position; and
updates the group identity database based on the manual adjustment.

16. A system for controlling at least one adjustable component of a vehicle, the system comprising:
at least one positioning actuator that adjusts the at least one adjustable component;
an adjustment control system that controls the at least one positioning actuator;
a group identity database storing target position data corresponding to at least one target position for the at least one adjustable component, wherein the group identity database includes a plurality of group identity profiles associated with identification information of a target occupant; and
at least one controller:
that receives occupant data, the occupant data including demographic information corresponding to a plurality of occupants of the vehicle;
that receives trip data, the trip data including travel route information and occupancy information, wherein the travel route information corresponds to a projected travel route and the occupancy information corresponds to at least one of a number of the plurality of occupants, an identity of the target occupant, and a position of the one or more of the plurality of occupants;
that determines a current group identity profile of the plurality of group identity profiles based on the occupancy information;
that communicates the occupant data and the trip data to the group identity database;
that receives, from the group identity database, the target position data determined based on the occupant data and the trip data; and
that communicates, via the adjustment control system, an instruction to position the at least one adjustable component toward the at least one target position.

17. The system for controlling at least one adjustable component of a vehicle of claim 16, wherein the at least one adjustable component is at least one vehicle seat.

18. The system for controlling at least one adjustable component of a vehicle of claim 17, wherein the at least one controller controls the at least one positioning actuator to adjust the vehicle seat toward the at least one target position.

19. The system for controlling at least one adjustable component of a vehicle of claim 16, wherein the at least one controller comprises a controller on a personal mobile device of the at least one occupant and a local controller of the vehicle.

* * * * *